US008703824B2

(12) United States Patent
Srinivas et al.

(10) Patent No.: US 8,703,824 B2
(45) Date of Patent: Apr. 22, 2014

(54) CATIONIC AMPHIPHILES WITH MANNOSE-MIMICKING HEAD-GROUPS AND A PROCESS FOR THE PREPARATION THEREOF

(75) Inventors: Ramishetti Srinivas, Hyderabad (IN); Arup Garu, Hyderabad (IN); Sachin B. Agawane, Hyderabad (IN); Arabinda Chaudhuri, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 13/812,703

(22) PCT Filed: Sep. 14, 2011

(86) PCT No.: PCT/IN2011/000629
§ 371 (c)(1),
(2), (4) Date: Jan. 28, 2013

(87) PCT Pub. No.: WO2012/035557
PCT Pub. Date: Mar. 22, 2012

(65) Prior Publication Data
US 2013/0129758 A1    May 23, 2013

(30) Foreign Application Priority Data
Sep. 14, 2010    (IN) .......................... 2170/DEL/2010

(51) Int. Cl.
*A01N 37/18*    (2006.01)
*A61K 31/165*   (2006.01)
*A61K 31/16*    (2006.01)
*C07C 233/00*   (2006.01)
*C07C 235/00*   (2006.01)
*C07C 237/00*   (2006.01)
*C07C 239/00*   (2006.01)

(52) U.S. Cl.
USPC ........... 514/623; 514/626; 514/627; 564/191; 564/197; 564/295

(58) Field of Classification Search
USPC ................. 514/622, 623; 424/184.1; 564/191
See application file for complete search history.

(56) References Cited

U.S. PATENT DOCUMENTS

| 4,897,355 A | 1/1990 | Eppstein et al. |
| 4,946,787 A | 8/1990 | Eppstein et al. |

(Continued)

FOREIGN PATENT DOCUMENTS

| WO | 2008/001166 A2 | 1/2008 |
| WO | 2009/109996 A2 | 9/2009 |

OTHER PUBLICATIONS

Priya P. Karmali, Valluripalli V. Kumar, and Arabinda Chaudhuri; J. Med. Chem. 2004, 47, 2123-2132.*

(Continued)

*Primary Examiner* — John Mabry
*Assistant Examiner* — Daniel Carcanague
(74) *Attorney, Agent, or Firm* — Ladas & Parry LLP

(57) ABSTRACT

The present invention discloses novel cationic amphiphiles containing mannose-mimicking shikimic and quinic acid head-groups and a process for preparing cationic amphiphiles with mannose-mimicking polar head-groups such as, shikimic and quinic acids. The findings described herein also demonstrate that compounds of the present invention can target model DNA vaccines to antigen presenting cells (APCs) such as macrophages and dendritic cells (DCs), via mannose receptors expressed on the cell surface of APCs. The cationic amphiphiles disclosed herein show enhanced cellular and humoral immune response compared to their mannosyl counterpart in dendritic cell (DC, the most professional APC) based genetic immunization in mice. Cationic amphiphiles with mannose-mimicking quinic and shikimic acid head-groups described in the present invention are likely to find future applications in the field of genetic immunization.

20 Claims, 8 Drawing Sheets

(56) References Cited

U.S. PATENT DOCUMENTS

| | | | |
|---|---|---|---|
| 5,264,618 | A | 11/1993 | Felgner et al. |
| 5,283,185 | A | 2/1994 | Epand et al. |
| 5,527,928 | A | 6/1996 | Nantz et al. |
| 5,614,503 | A | 3/1997 | Chaudhary et al. |
| 5,661,018 | A | 8/1997 | Ashley et al. |
| 5,686,620 | A | 11/1997 | Ashley et al. |
| 5,688,958 | A | 11/1997 | Ashley et al. |
| 5,698,721 | A | 12/1997 | Heath |
| 5,705,693 | A | 1/1998 | DePrince et al. |
| 5,719,131 | A | 2/1998 | Harris et al. |
| 6,503,945 | B2 | 1/2003 | Banerjee et al. |
| 6,541,649 | B2 | 4/2003 | Banerjee et al. |
| 7,157,439 | B2 | 1/2007 | Boudreau et al. |
| 7,166,298 | B2 | 1/2007 | Jessee et al. |
| 8,278,483 | B2 | 10/2012 | Mahidhar et al. |

OTHER PUBLICATIONS

Omid Akbari, et al; "DNA Vaccination: Transfection and Activation of Dendritic Cells as Key Events for Immunity", Journal of Experimental Medicine, vol. 189, No. 1, Jan. 4, 1999, pp. 169-177.

Jacques Banchereau, et al; "Dendritic cells and the control of immunity", Nature, vol. 392, Mar. 19, 1998, p. 245-252.

Michael A. Chattergoon, et al; "Specific Immune Induction Following DNA-Based Immunization Through In Vivo Transfection and Activation of Macrophages/Antigen-Presenting Cells", The Journal of Immunology, vol. 160, Issue 12, pp. 5707-5718, Jun. 15, 1998.

Pascale Chenevier, et al; "Grafting of synthetic mannose receptor-ligands onto onion vectors for human dendritic cells targeting", Chemical Communications, Issue 20, pp. 2446-2447, First published on the web Sep. 25, 2002

Ronald N. Germain; "MHC-Dependent Antigen Processing and Peptide Presentation: Providing Ligands for T Lymphocyte Activation", Cell, vol. 76, Jan. 28, 1994, pp. 287-299.

Cyrille Grandjean, et al; "Novel Hyperbranches Glycomimetics Recognized by the Human Mannose Receptor: Quinic or Shikimic Acid Derivatives as Mannose Bioisosteres", Chembiochem, vol. 2, Issue 10, pp. 747-757, Oct. 1, 2001.

Gregory Gregoriadis, et al; "Liposome-mediated DNA vaccination", FEBS Letters, vol. 402, Issue 2, pp. 107-110, Jan. 27, 1997.

Sanjay Gurunathan, et al; "DNA VACCINES: Immunology, Application, and Optimization", Annual Reviews Immunology, vol. 18, pp. 927-974, Apr. 2000.

Yoshiyuki Hattori, et al; "Enhancement of immune responses by DNA vaccination through targeted gene delivery using mannosylated cationic liposome formulation following intravenous administration in mice", Biochemical and Biophysical Research Communications, vol. 317, Issue 4, pp. 992-999, May 14, 2004.

Mary Lynne Hedley, et al; "Microspheres containing plasmid-encoded antigens elicit cytotoxic T-cell responses", Nature Medicine, vol. 4, No. 3, Mar. 1998, pp. 365-368.

Alistair S. Irvine, et al; "Efficient nonviral transfection of dendritic cells and their use for in vivo immunization", Nature Biotechnology, vol. 18, Dec. 2000, pp. 1273-1278.

Kin J. Ishii, et al; "TANK-binding kinase-1 delineates innate and adaptive immune responses to DNA vaccines", Nature Letters, vol. 451, Feb. 7, 2008, p. 725-730.

Priya Prakash Karmali, et al; "Cationic Liposomes as Non-Viral Carriers of Gene Medicines: Resolved Issues, Open Questions, and Future Promises", Medicinal Research Reviews, vol. 27, No. 5, pp. 696-722, Article first published online: Oct. 4, 2006.

Linda S. Klavinskis, et al; "Mucosal immunization with DNA-liposome complexes", Vaccine, vol. 15, No. 8, pp. 818-820, Jun. 1997.

M.A. Liu; "DNA vaccines: a review", Journal of Internal Medicine, vol. 253, Issue 4, pp. 402-410, Apr. 2003.

Margaret A. Liu, et al; "Immunization of non-human primates with DNA vaccines", Vaccine, vol. 15, No. 8, pp. 909-912, Jun. 1997.

Yan Lu, et al; "Development of an antigen-presenting cell-targeted DNA vaccine against melanoma by mannosylated liposomes", Biomaterials, vol. 28, pp. 3255-3262, Jul. 1, 2007.

Yvonne Perrie, et al; "Liposome-mediated DNA vaccination: the effect of vesicle composition", Vaccine, vol. 19, Issues 23-24, Apr. 30, 2001, pp. 3301-3310.

Jason Rice et al; "DNA vaccines: precision tools for activating effective immunity against cancer", Nature Reviews Cancer, vol. 8, pp. 108-120, Feb. 2008.

Steven A. Rosenberg, et al; "Inability to Immunize Patients with Metastatic Melanoma Using Plasmid DNA Encoding the gp100 Melanoma-Melanocyte Antigen", Hum Gene Ther., May 20, 2003; vol. 14(8), pp. 709-714.

Michael J. Roy, et al; "Induction of antigen-specific CD8 + T cells, T helper cells, and protective levels of antibody in humans by particle-mediated administration of a hepatitis B virus DNA vaccine", Vaccine, vol. 19, Issues 7-8, Nov. 22, 2000, pp. 764-778.

Federica Sallusto, et al; "Dendritic Cells Use Macropinocytosis and the Mannose Receptor to Concentrate Macromolecules in the Major Histocompatibility Complex Class II Compartment: Downregulation by Cytokines and Bacterial Products", J. Exp. Med, vol. 182, Aug. 1995, pp. 389-400.

Manmohan Singh, et al; "Cationic microparticles: A potent delivery system for DNA vaccines", PNAS, vol. 97, No. 2, Jan. 18, 2000, pp. 811-816.

Ramishetti Srinivas, et al; "Cationic amphiphiles: promising carriers of genetic materials in gene therapy", Chemical Society Review, vol. 38, pp. 3326-3338, First published as an Advance Article on the web Jul. 8, 2009.

Ramishetti Srinivas, et al; "Cationic Amphiphile with Shikimic Acid Headgroup Shows More Systemic Promise Than Its Mannosyl Analogue as DNA Vaccine Carrier in Dendritic Cell Based Genetic Immunization", Journal of Medicinal Chemistry, vol. 53, pp. 1387-1391, Published on Web, Jan. 5, 2010.

Ralph M. Steinman; "The Dendritic Cell System and Its Role in Immunogenicity", Annual Review Immunol., vol. 9, pp. 271-296, Apr. 1991.

S. Toda, et al; "HIV-1-specific cell-mediated immune responses induced by DNA vaccination were enhanced by mannan-coated liposomes and inhibited by anit-interferon-γ antibody", Immunology, vol. 92, pp. 111-117, Sep. 1997.

Jeffrey B. Ulmer, et al; "Protective immunity by intramuscular injection of low doses of influenza virus DNA vaccines", Vaccine, vol. 12, No. 16, Dec. 1994, pp. 1541-1544.

Robert G. Whalen, et al; Short Analytical Review DNA-Mediated Immunization and the Energetic Immune Response to Hepatitis B Surface Antigen, Clinical Immunology and Immunopathology, vol. 75, No. 1, Apr. 1995, pp. 1-12.

Wassana Wijagkanalan, et al; "Efficient targeting to alveolar macrophages by intratracheal administration of mannosylated liposomes in rats", Journal of Controlled Release, vol. 125, pp. 121-130, Available online Oct. 22, 2007.

International Search Report; mailed Jan. 1, 2012; PCT/IN2011/000629.

Jiin H. Felgner, et al; "Enhanced Gene Delivery and Mechanism Studies with A Novel Series of Cationic Lipid Formulations", The Journal of Biological Chemistry, vol. 269, No,4, Issue of Jan. 28, 1994, pp. 2550-2561.

Philip L. Felgner, et al; "Lipofection: A highly efficient, lipid-mediated DNA-transfecton procedure", Pro. Natl. Acad. Sci., USA, vol. 84, pp. 7413-7417; Nov. 1987.

(56) References Cited

OTHER PUBLICATIONS

VV Kumar, et al; "Single histidine residue in head-group region is sufficient to impart remarkable gene transfection properties to cationic lipids: evidence for histidine-mediated membrane fusion at acidic pH", Gene Therapy, vol. 10, pp. 1206-1215; Aug. 2003.

Rania Leventis, et al; "Interactions of mammalian cells with lipid dispersions containing novel metabolizable cationic amphiphiles", Biochimica et Biophysica Acta, vol. 1023, pp. 124-132; Mar. 30, 1990.

P. Schoen, et al; "Gene transfer mediated by fusion protein hemagglutinin reconstituted in cationic lipid vesicles", Gene Therapy, vol. 6, pp. 823-832; May 1999.

Igor Solodin, et al; "A Novel Series of Amphiphilic Imidazolinium Compounds for in Vitro and in Vivo Gene Delivery", Biochemistry, vol. 34, pp. 13537-13544; Oct. 17, 1995.

Carl J. Wheeler, et al; "A novel cationic lipid greatly enhances plasmid DNA delivery and expression in mouse lung", Proc. Natl Acad. Sci., USA, vol. 93, pp. 11454-11459, Oct. 1996.

* cited by examiner

Scheme 1: Synthesis of cationic Amphiphiles (X) with mannose-mimicking Shikimic Acid Head group:

Scheme 2: Synthesis of Cationic Amphiphiles (Y) With mannose-mimicking Quinic Acid Head Group:

Scheme 3: Synthesis of Cationic Amphiphle 3 with Mannosyl Head group:

CATIONIC AMPHIPHILES WITH MANNOSE-MIMICKING HEAD-GROUPS AND A PROCESS FOR THE PREPARATION THEREOF

FIELD OF THE INVENTION

The present invention relates to novel cationic amphiphiles containing mannose-mimicking shikimic and quinic acid head-groups. More particularly, the present invention provides a process for preparing these cationic amphiphiles containing mannose-mimicking shikimic and quinic acid head-groups. Further, the invention provides novel compositions containing the said cationic amphiphiles with mannose-receptor specific gene transfer properties. The liposomal formulations of the cationic amphiphiles described herein are capable of for targeting DNA vaccines to antigen presenting cells (APCs) in genetic immunization. The cationic amphiphiles disclosed herein show enhanced cellular and humoral immune response compared to their mannosyl counterpart in dendritic cell (DC, the most professional APC) based genetic immunization in mice. The area of medical science that is likely to benefit most from the present invention is dendritic cell based genetic immunization.

BACKGROUND OF THE INVENTION

Development of vaccines is a remarkable triumph of medical science. Traditional vaccines consist of protein antigens from pathogens, live attenuated viruses, or killed bacteria. However, the protein antigens are sometimes not efficient in mounting cellular immune responses (e.g. induction of cytotoxic T-lymphocytes, CTLs) which is one of the most sought after components for vaccines. To this end, more recently, DNA vaccination, the administration of antigen encoded DNA, is gaining increasing attention as an emerging therapeutic approach for the treatment of many complex disorders including cancer, infectious disease, and allergies (Ishii, K. J. et al. Nature 2008; 451:725-729, Rice, J. et al. Nat. Rev. Cancer. 2008; 8:108-120). DNA vaccines are capable of inducing both humoral and cellular immune responses and are regarded as potentially safer than their attenuated virus counterparts (Gurunathan, S. et al. Annu. Rev. Immunol. 2000; 18:927-974, Liu, M. A. J. Int. Med. 2003; 253:402-410).

Since the pioneering report by Wolff et al. in 1991 on the use of naked DNA in transfecting muscle cells in vivo (Wolff, J. A. et al. Science 1991; 247:1465-1468), several studies have shown that intramuscular injection of a specific antigen encoded naked plasmid DNA can trigger humoral and cell mediated protective immunity against the antigen (Whalen, R. G. et al. Clin. Immunol Immunopathol. 1995; 75:1-12, Ulmer, J. B. et al. Vaccine 1994; 12:1541-1544, Liu, M. A. et al. Vaccine 1997; 15:909-912, Gurunathan, S. et al. Annu. Rev. Immunol. 2000; 18:1297-1306, Liu, M. A. J. Int. Med. 2003; 253:402-4104-6). However, clinical trials have revealed that the immune response induced by a topical injection of naked DNA is insufficient (Roy, M. J. et al. Vaccine, 2000; 19:764-778, Rosenberg, S. A. et al. Hum. Gene Ther. 2003; 14:709-714). Studies have shown that transfection and subsequent activation of antigen presenting cells (APC) such as dendritic cells (DC) and macrophages are key events in the development of immunity following genetic immunization (Akbari, O. et al. J. Exp. Med. 1999; 189:169-178, Chattergon, M. A. et al. J. Immunol. 1998; 160: 5707-5718). Mountain and co-workers demonstrated that immunization of mice with monocyte-derived dendritic cells transfected with a complex of cationic peptide and a gene encoding tumor associated antigens protected the mice from a lethal challenge with melanoma cells (Irvine, A. S. et al. Nat. Biotechnol. 2000; 18:1273-1278).

Antigen presenting cells such as dendritic cells and macrophages process the antigenic protein through their proteasome complexes into small peptide fragments. These small peptide fragments are then presented to the immune cells (CD8+ and CD4+ T cells) via MHC class I and MHC class II molecules resulting in the induction of cytotoxic T lymphocyte (CTL) and humoral responses (Steinman, R. M. Annu. Rev. Immunol. 1991; 9: 271-296, Banchereau, R. M. and Steinman, R. M. Nature 1998; 392:245-252, Germain, R. N. Cell 1994; 76:287-299, Akbari, O. et al. J. Exp. Med. 1999; 189:169-178, Chattergon, M. A. et al. J. Immunol. 1998; 160:5707-5718, Banchereau, J. and Steinman, R. M. Nature 1998; 392: 245-252). However, antigen presenting cells are hard to transfect. Use of cationic microparticles (Hedley, M. L. et al. Nat. Med. 1998; 4:365-368; Singh, M. et al. Proc. Natl. Acad. Sci. USA 2000; 97:811-816), cationic liposomes (Perrie, Y. et al. Vaccine 2001; 19:3301-3310), and cationic peptide (Irvine, A. S. et al. Nat Biotechnol 2000; 18:1273-1278), etc. have previously been reported for direct transfection of APCs in DNA vaccination. Attempts have been made to increase the potency of immune response through direct transfection of APCs by delivering the antigen encoding DNA via cationic liposomes (Gregoriadis, G. et al. FEBS Lett. 1997; 402:107-110, Klavinskis, L. S. et al. Vaccine 1997; 15: 818-820, Perrie, Y. et al. Vaccine 2001; 19:3301-3310, Hattori, y. et al. Biochem. Biophys. Res. Comm. 2004; 317:992-999). Cationic liposomes owing to their non-toxic and bio-compatible nature offer great advantage over other means of DNA delivery. A greater degree of control can be exercised over the lipid's structure on a molecular level and the products can be highly purified. Use of cationic liposomes does not require any special expertise in handling and preparation techniques. Cationic liposomes can be covalently grafted with receptor specific ligands for accomplishing targeted gene delivery. Such multitude of favorable clinical features are increasingly making cationic liposomes as the non-viral transfection vectors of choice for delivering genes into body cells (Karmali, P. P. and Chaudhuri, A. Med. Res. Rev. 2007; 27: 696-722; Srinivas, R. et al. Chem. Soc. Rev. 2009; 38:3326-3338; U.S. Pat. Nos. 4,897,355 and 4,946,787 (1990); U.S. Pat. No. 5,264,618 (1993); U.S. Pat. No. 5,283,185 (1994); U.S. Pat. No. 5,283,185 (1994); U.S. Pat. No. 5,527,928 (1996); U.S. Pat. No. 5,698,721 (1997); U.S. Pat. Nos. 5,661,018; 5,686,620 and 5,688,958 (1997); U.S. Pat. No. 5,614,503 (1997); U.S. Pat. No. 5,705,693 (1998); U.S. Pat. No. 5,719,131 (1998); U.S. Pat. No. 5,527,928, (1996); U.S. Pat. No. 6,541,649 (2003); U.S. Pat. No. 6,503,945 (2003); U.S. Pat. No. 7,157,439 (2007). In U.S. Pat. No. 7,166,298 (2007), Jessee J. A. and Hearl W. G. disclosed a method for genetic immunization using compositions comprising cationic lipids and antigen encoded DNA.

A promising approach for enhancing the efficacy of DNA vaccination is based on targeting DNA vaccines to APCs via mannose receptor, a 180 kDa multi-domains unique transmembrane receptors expressed on their cell surfaces (Sallusto, F. et al. J. Exp. Med. 1995; 182:389-400). For instance, use of mannan (a ligand for the mannose receptor) coated liposomes for intranasal delivery of HIV-1 DNA vaccine (Toda, S. et al. Immunology 1997; 92:111-117), mannan-coated cationic nanoparticles for topical immunization (Cui, Z. and Mumper, R. J. J. Control. Rel. 2002; 81:173-184) and mannosylated cationic liposomes have been reported for delivering DNA vaccine to APCs (Hattori, Y. et al. Biochem.

Biophys. Res. Comm 2004; 317: 992-999, Wijagkanalan, W. et al. J. Control. Rel. 2008; 125:121-130, Lu Y. et al. Biomaterials 2007; 28:3255-3262). Grandjean and coworkers have previously demonstrated that lysine based clusters of mannose mimicking carbocyclic acids such as quinic and shikimic acid are also effective ligands for the mannose receptor of dendritic cells (Grandjean, C. et al. Chem. biochem 2001; 2:747-757, Chenevier, P. et al. Chem. Commun. (comb) 2002; 20:2446-2447). Very recently, Srinivas, R. et al. has shown that cationic amphiphiles with mannose-mimicking quinic and shikimic acid head-groups can target DNA to antigen presenting cells via mannose receptors (Srinivas, R. et al. J. Med. Chem. 2010; 53:1387-1391). This previous work demonstrated that subcutaneous administration of DCs pre-transfected with electrostatic complex of DNA encoded therapeutic MART1 antigen (antigen of human melanoma tumor) and liposomes of cationic amphiphile with shikimic acid head-group provides more tumor protective effect in C57BL/6 mice challenged with aggressive B16F1 melanoma tumor than subcutaneous administration of the corresponding lipoplex of mannosylated cationic glycolipid (Srinivas, R. et al. J. Med. Chem. 2010; 53:1387-1391). However, the efficiencies of dendritic cells transfection by the liposomes prepared from cationic amphiphiles with mannose-mimicking shikimic and quinic acid head-groups were poor (~3%, Srinivas, R. et al. J. Med. Chem. 2010; 53:1387-1391). Contrastingly, the efficiencies of DC-transfection by the liposomal formulations of the cationic amphiphiles described herein are about 3-4 fold higher (transfection efficiency within the range of 10-12%). Lipids covered in our previously applied patents applications (Indian Patent Application No. 359/DEL/2006; International Patent Application No. PCT/IB 2007/000281, Publication No. WO/2008/001166, Publication date: Mar. 1, 2008) are 3-4 fold less efficient than the presently described lipids in transfecting dendritic cells. In addition, the presently described novel cationic amphiphiles with mannose-mimicking head-groups are efficacious in eliciting both cellular and humoral immune responses in dendritic cell based genetic immunization in mice and are therefore likely to find future applications in the area of DNA vaccination.

OBJECTS OF THE INVENTION

The main object of the present invention is to provide novel cationic amphiphiles containing mannose-mimicking shikimic and quinic acid head-groups.

Another object of the present invention is to provide a process for the synthesis of novel cationic amphiphiles containing mannose-mimicking shikimic and quinic acid head-groups for efficient delivery of genetic materials into antigen presenting cells.

Another objective of the present invention is to show that the cellular uptake of the complex of liposomes of the presently described cationic amphiphiles and model. DNA vaccine is mediated by the mannose receptors of the antigen presenting cells.

Another objective is to demonstrate that the presently described systems can produce immune response in mice in dendritic cell based genetic immunization using a model DNA vaccine.

Another objective of the present invention is to show that the complex of the liposomes prepared with the presently described cationic amphiphiles with mannose-mimicking head-groups and the model DNA vaccine elicit enhanced cellular and humoral immune responses compared to those elicited by the complexes of liposomes prepared with the corresponding mannosyl counterparts.

SUMMARY OF THE INVENTION

Accordingly, the present invention provides cationic amphiphiles with mannose-mimicking acid head-groups having the general formula A

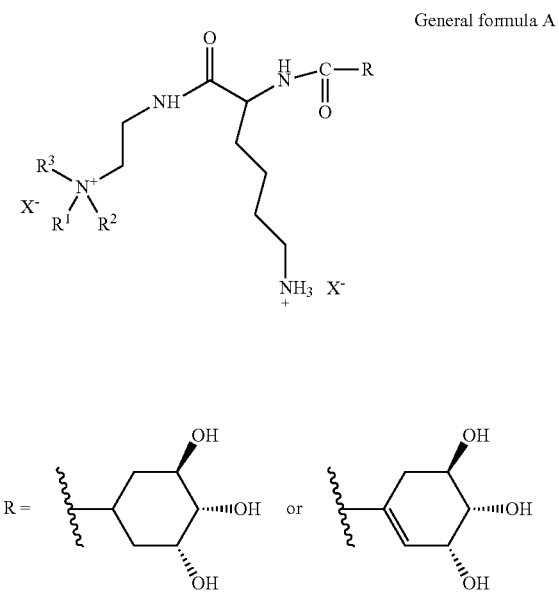

General formula A

Wherein each of $R^1$ and $R^2$ is independently hydrogen or a lipophilic moiety containing at least eight carbon atoms and is optionally selected from 8-24 carbon containing alkyl, mono-, di- and tri-unsaturated alkenyl ($C_8$-$C_{22}$) provided both $R^1$ and $R^2$ are not hydrogen;

$R^3$ is independently hydrogen or alkyl ($C_1$-$C_5$, straight or branched) or hydroxy or amino-alkyl functional groups ($C_1$-$C_5$, straight or branched);

X is optionally selected from chlorine or bromine atom.

In an embodiment of the present invention the cationic amphiphiles with mannose-mimicking acid head-groups of general formula A is represented by the compounds of general formulae 1 and 2

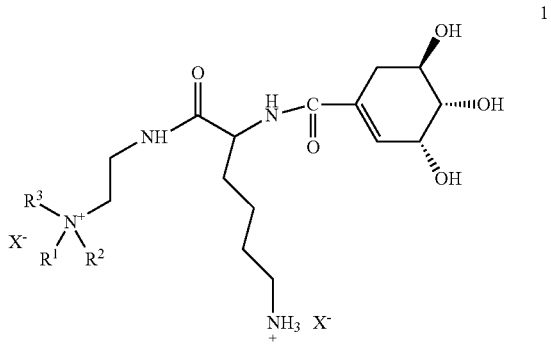

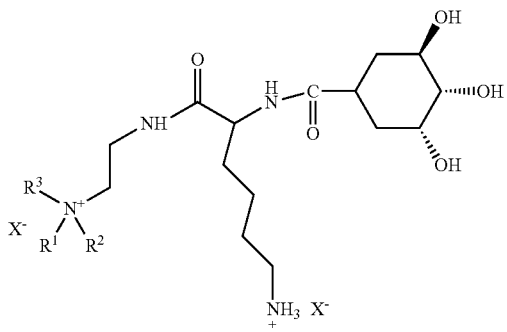

In another embodiment of the present invention lipophilic R1 and R₂ group are selected from the group consisting of saturated $C_8$-$C_{22}$ alkyl groups and unsaturated $C_8$-$C_{22}$ alkenyl groups containing 1, 2 or 3 double bonds.

In another embodiment of the present invention, a process for the synthesis of Cationic amphiphiles with mannose-mimicking acid head-groups of general formula A General formula A Wherein each of $R^1$ and $R^2$ is independently hydrogen or a lipophilic moiety containing at least eight carbon atoms and is optionally selected from 8-24 carbon containing alkyl, mono-, di- and tri-unsaturated alkenyl ($C_8$-$C_{22}$) provided both $R^1$ and $R^2$ are not hydrogen;

$R^3$ is independently hydrogen or alkyl ($C_1$-$C_5$, straight or branched) or hydroxy or amino-alkyl functional groups ($C_1$-$C_5$, straight or branched);

X is optionally selected from chlorine or bromine atom, said process comprising the steps of:
a. Coupling a mixed primary-tertiary lipophilic aliphatic alkyl protected amine containing saturated or unsaturated aliphatic hydrocarbon chains with shikimic or quinic acids in polar aprotic solvent, in presence of amide bond forming reagent selected from group ethylenedicarbodiimide (EDCI) and N-hydroxybenzotriazole (HOBt) at 0-80° C. to obtain the corresponding aliphatic hydrobhobic amide intermediate;

b. quaternizing the protected hydrophobic amide obtained in step (a) with excess of appropriate alkyl iodides to obtain the corresponding protected quaternized amphiphilic ammonium iodide intermediate;
c. deprotecting of protected quaternized amphiphilic ammonium iodide intermediate as obtained in step (b) followed by ion exchange chromatography on halide ion exchange resin and mixed polar organic solvent as the eluent to obtain compounds of general formula A.

In another embodiment of the present invention, saturated or unsaturated aliphatic hydrocarbon chains of the mixed primary-tertiary amine is selected from the group of 8-22 carbon atoms.

In another embodiment of the present invention, the polar aprotic solvent used in step (a) is selected from the group consisting of dichloro methane, dimethyl formamide, dimethylsulphoxide, pyridine, and triethyl amine.

In another embodiment of the present invention quaternization of the intermediate hydrophobic amide obtained in step (a) is carried out at a temperature between 25-30° C.

In another embodiment of the present invention, the organic solvent used as polar eluent in step (c) is selected from the group consisting of methanol, ethanol, chloroform, dichloro methane and ethyl acetate.

In another embodiment of the present invention, the halide ion exchange resins used in step (c) is selected from the chloride and bromide ion exchange resins.

Yet another embodiment of the invention provides a formulation comprising the cationic amphiphiles of claim 1, in pure form or in combination with co-lipids and polyanionic compounds preferably nucleic acids along with physiologically acceptable additives.

In another embodiment of the present invention, the co-lipid is selected from sterol group or a neutral phosphatidyl ethanolamine or neutral phosphatidyl choline.

In another embodiment of the present invention, the co-lipid is selected from the group consisting of cholesterol, dioleyolphosphatidylethanolamine (DOPE), and dioleyol-phosphatidylcholine (DOPC).

In another embodiment of the present invention, the co-lipid is preferentially selected from dioleyolphosphatidyl-choline (DOPC) or cholesterol.

In yet another embodiment of the present invention, the molar ratio of the cationic amphiphile to colipid used is in the range of 1:1 to 1:3, preferably 1:1.

In yet another embodiment of the present invention, the polyanionic compounds are biologically active compounds selected from the group comprising of nucleic acids that encode for a therapeutically important immunogen, protein, nucleic acid, an oligonucleotide, a peptide or a protein or a drug.

In yet another embodiment of the present invention, the nucleic acid is selected from the group of a circular or linear plasmid or is a ribonucleic acid, a ribosomal RNA, antisense polynucleotide of RNA or DNA, polynucleotide of genomic DNA, cDNA or mRNA.

In yet another embodiment of the present invention, the polyanionic compounds are used singly or in combination thereof.

In yet another embodiment of the present invention, the said formulations are administered via cutaneous, sub-cutaneous, intradermal, nasal, intravenous, intramuscular, intra-peritonial or pulmonary route.

In yet another embodiment of the present invention, the said formulation is administered intracellularly in the range of 25 to 100 microliters.

In yet another embodiment of the present invention, the said formulation is administered to cells at a ratio 0.1 to 0.5 microgram of DNA to 50,000 cells.

In yet another embodiment of the present invention, the said formulation comprises amount of cationic amphiphiles in the range of 9.0 to 0.3 microgram and lipid to DNA charge ratios ranging from 0.3:1 to 9:1.

Still another embodiment of the invention provides a formulation for use in the delivery of biologically active compounds into antigen presenting cells in genetic immunization.

Still another embodiment of the invention provides a transfection complex comprising of the formulation as claimed in claim 10.

In another embodiment of the present invention, a method for producing immune response, comprising: (a) administering the transfection complex containing of least one cationic amphiphiles with a polynucleotide wherein the said polynucleotide encodes an immunogen to at least one mouse thereby generating at least one immunized mouse; (b) measuring the monoclonal antibodies produced in mouse body.

Reagents: i) BOC-Lys(Z)—OH, EDCI, HOBt, dry DCM; ii) Pd(OH)$_2$/C, MeOH, HCl, H2; iii) EDCI, HOBt, dry DCM; iv) MeI/DCM (1:1), room temperature, 3 h; v) K2CO3, MeOH, Amberlite IR120 for H+ion exchange; vi) TFA:DCM (1:2), 0° C.; vii) Amberlyst A-26 for Cl-ion exchange.

Figure 1:
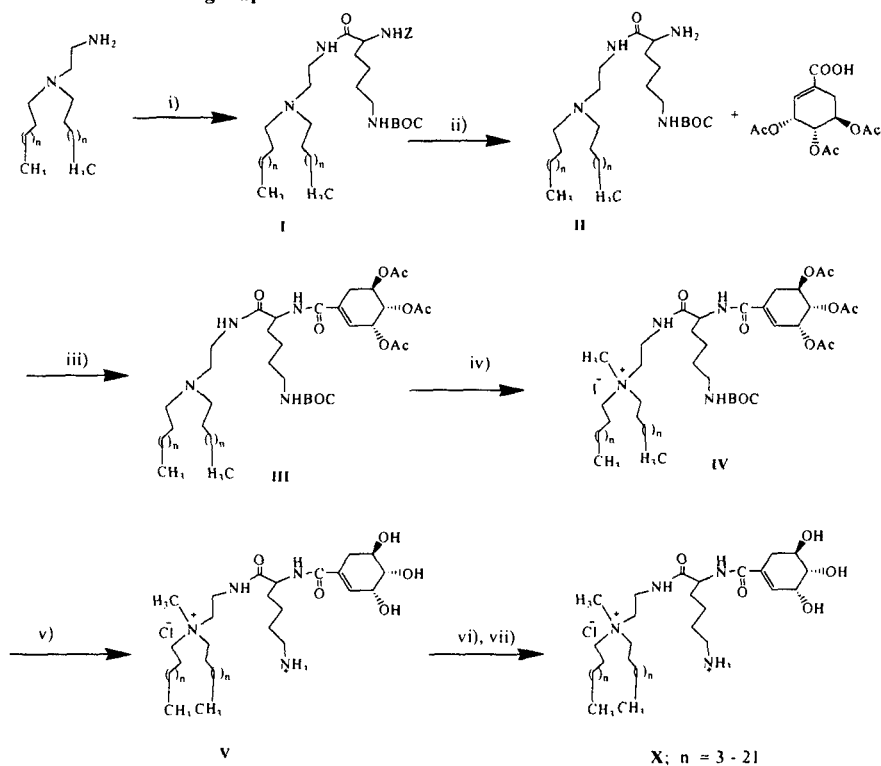
FIG. 1 is a schematic representation of the synthetic procedures used for the preparation of cationic amphiphiles containing mannose-mimicking shikimic acid head-groups (Scheme 1).
Figure 2:
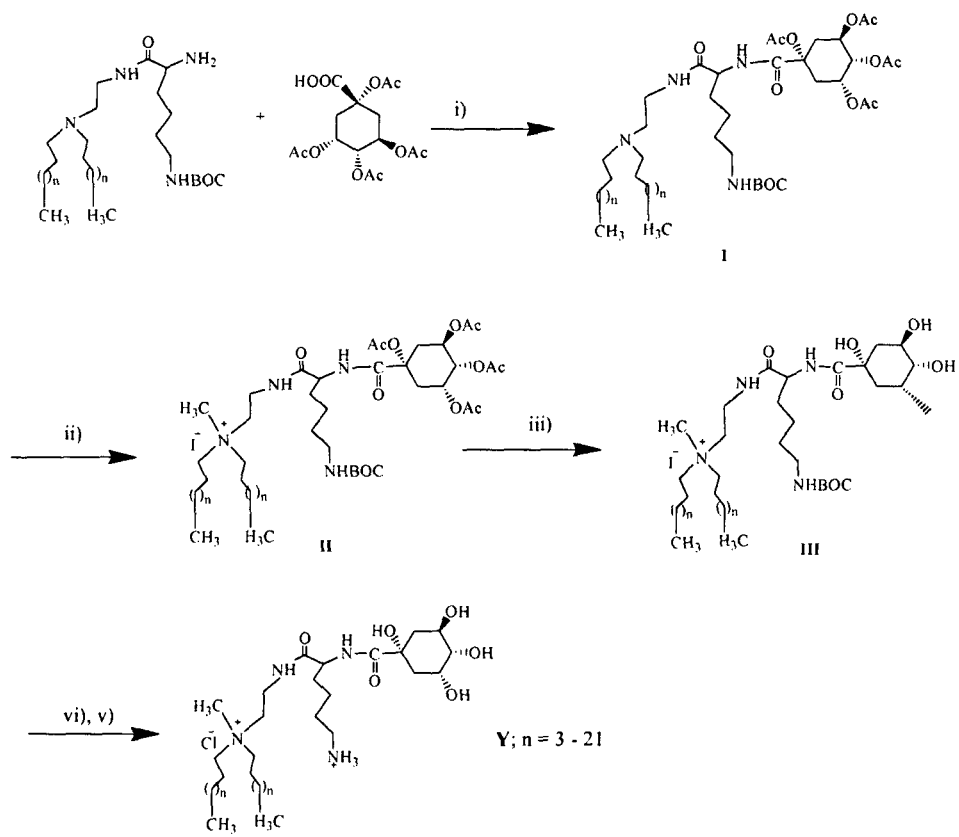

FIG. 2 is a schematic representation of the synthetic procedures used for the preparation of cationic amphiphiles containing mannose-mimicking quinic acid head-groups (Scheme 2).

Reagents: i) EDCI, HOBt, dry DCM; i) MeI/DCM (1:1), 0° C., 3 h; iii) $K_2CO_3$, MeOH, Amberlite IR120 for H+ion exchange; iv) TFA:DCM (1:2), 0° C.; v) Amberlyst A-26 for Cl-ion exchange.

Figure 3:
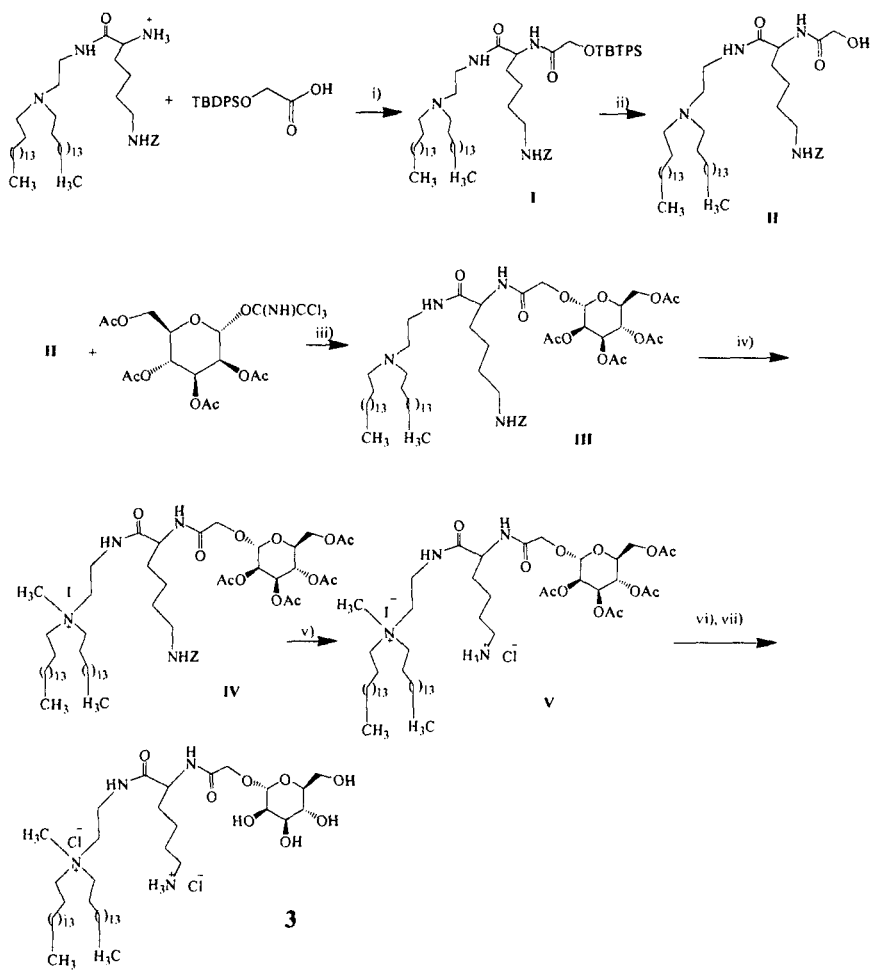

FIG. 3 is a schematic representation of the synthetic procedures used for the preparation of cationic amphiphile 3 containing a mannosyl head-group (Scheme 3).

Figure 4:
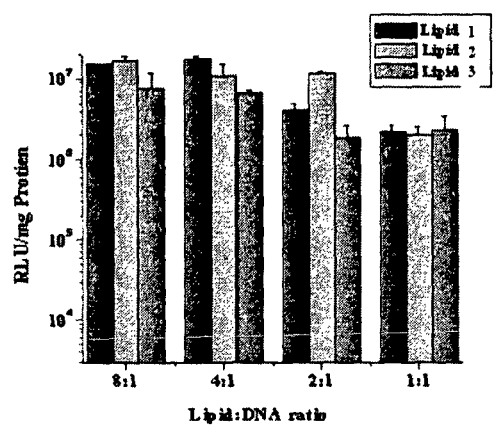

Reagents: i) EDC, HOBt, dry DCM; ii) TBAF, dry THF (iii) BF3OEt2, DCM, −20° C., 2 h; (iv) MeI, CHCl3, MeOH, overnight v) Pd(OH)$_2$, AcOH, HCl, MeOH, 15 h; vi) K2CO3, MeOH, Amberlite IR120 for H+ion exchange; vii) Amberlyst A-26 for Cl-ion exchange FIG. 4 summarizes the transfection efficiencies of 2-[(N,N-di-n-hexadecyl-N-methyl)amino]-ethylL-L-lysyl-shikimate chloride (lipid 1), 2-[(N,N-di-n-hexadecyl-N-methyl)amino]-ethylL-L-lysyl-quinate chloride (lipid 2) & 2-[(N,N-di-n-hexadecyl-N-methyl)amino]-ethylL-L-lysyl-β-D-Mannoside chloride (lipid 3) in RAW 264.7 cells in combination with DOPE (dioleoylphosphatidylethanolamine) as co-lipid across lipid:DNA charge ratios of 8:1-1:1 using pCMV-Luc as the reporter gene.

Figure 5:
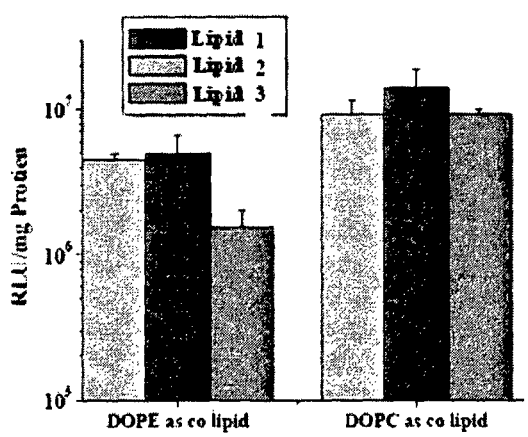

FIG. 5 summarizes the relative transfection efficiencies of lipids 1, 2 & 3 in RAW 264.7 cells when used in combination with DOPE and DOPC (dioleoylphosphatidylcholine) as co-lipids across lipid:DNA charge ratios of 8:1-1:1 using pCMV-Luc as the reporter gene.

Figure 6:
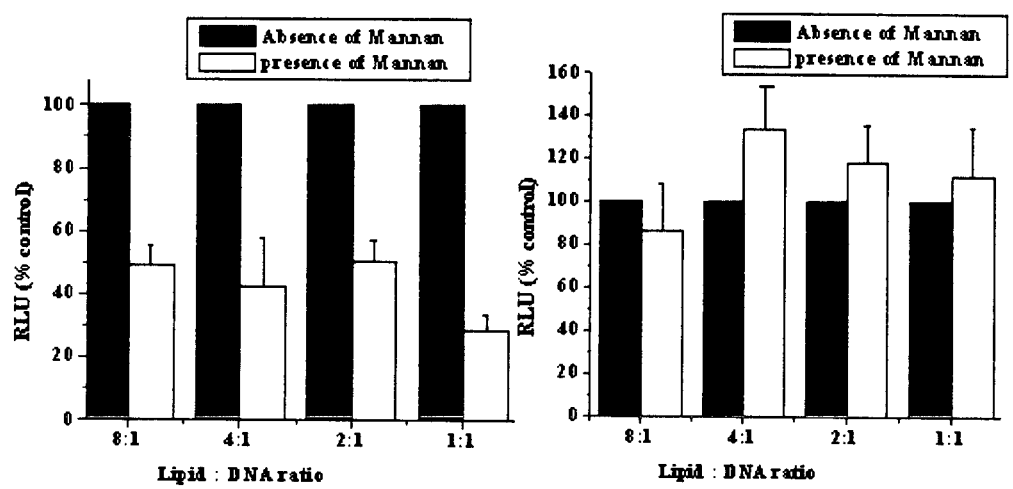

FIG. 6 summarizes transfection efficiencies of cationic amphiphile 1 with DOPE as co-lipid in the presence of 50 μg of mannan across the lipid:DNA ratio 8:1 to 1:1 in RAW cells (left) and in NIH3T3 cells (right). Percent control values refer to the relative luciferase activities compared to values in absence of mannan. The relative light units obtained for cells treated with the lipoplexes of cationic amphiphile 1 in the absence of mannan were taken to be 100.

Figure 7:
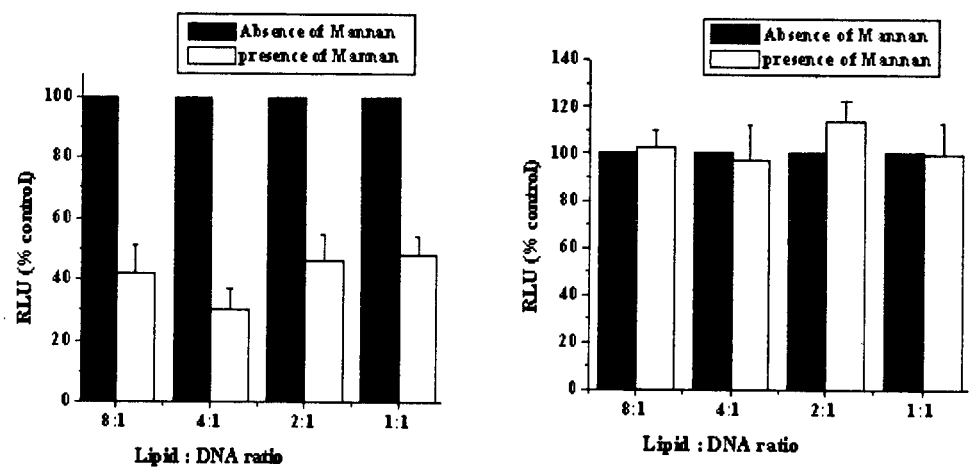

FIG. 7 depicts transfection efficiencies of cationic amphiphile 2 with DOPE as co-lipid in the presence of 50 μg of mannan across the lipid:DNA ratio 8:1 to 1:1 in RAW cells (left) and in NIH3T3 cells (right). Percent control values refer to the relative luciferase activities compared to values in absence of mannan. The relative light units obtained for cells treated with the lipoplexes of cationic amphiphile 2 in the absence of mannan were taken to be 100.

Figure 8:
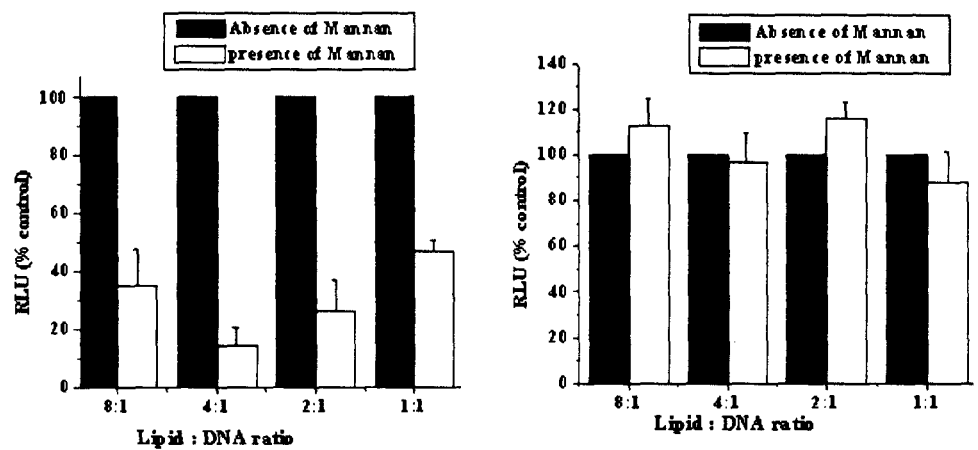

FIG. 8 summarizes transfection efficiencies of the mannosylated cationic amphiphile 3 with DOPE as co-lipid in the presence of 50 μg of mannan across the lipid:DNA ratio 8:1 to 1:1 in RAW cells (left) and in NIH3T3 cells (right). Percent control values refer to the relative luciferase activities compared to values in absence of mannan. The relative light units obtained for cells treated with the lipoplexes of mannosylated cationic amphiphile 3 in the absence of mannan were taken to be 100.

Figure 9:
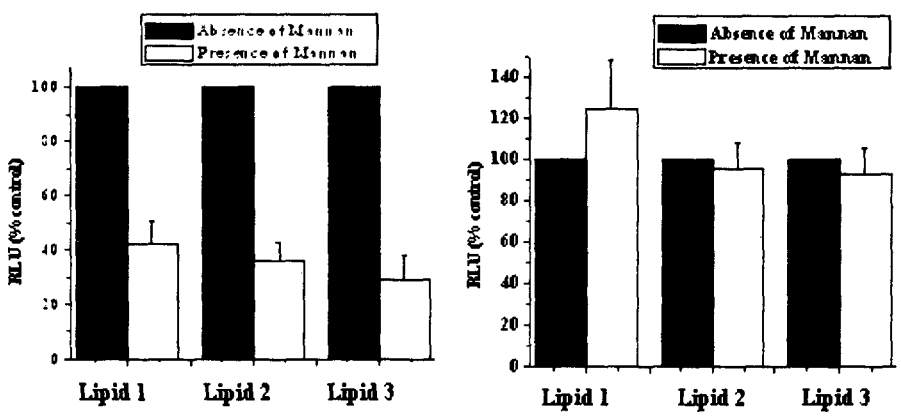

FIG. 9 summarizes transfection efficiencies of lipids 1, 2 & 3 with DOPC as co-lipid in the presence of 50 μg of mannan at 8:1 lipid:DNA ratio in RAW cells (left) and in NIH3T3 cells (right). Percent control values refer to the relative luciferase activities compared to values in absence of mannan. The relative light units obtained for cells treated with the lipoplexes in the absence of man-BSA were taken to be 100.

Figure 10:
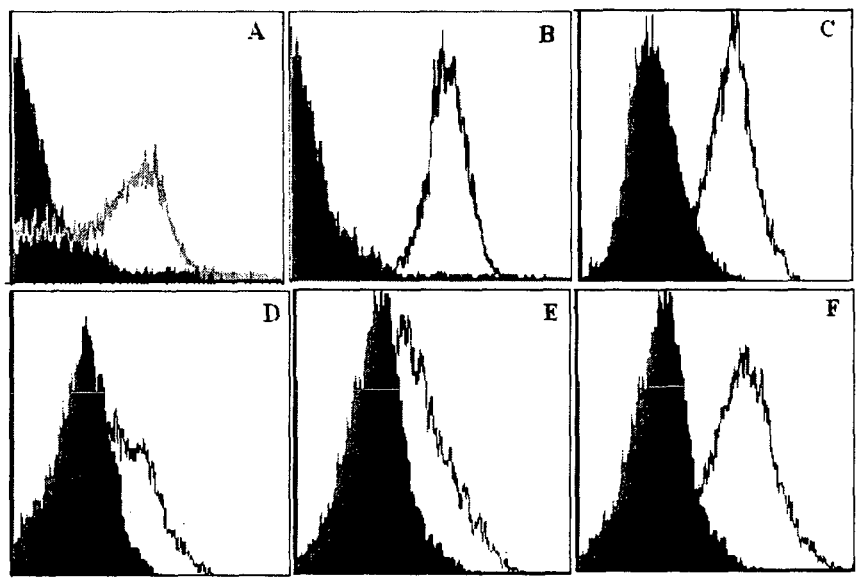

FIG. 10 depicts the FACS profile for immature mbmDC surface markers. mbmDCs were stained with FITC conjugated monoclonal antibodies specific for the cell surface MHC II (A), total MHC II (B, total of surface & intracellular MHC II), and Phycoerythrin conjugated monoclonal antibodies for Mannose receptor (C), CD11c (D), CD86 (E) and CD40 (F).

Figure 11:
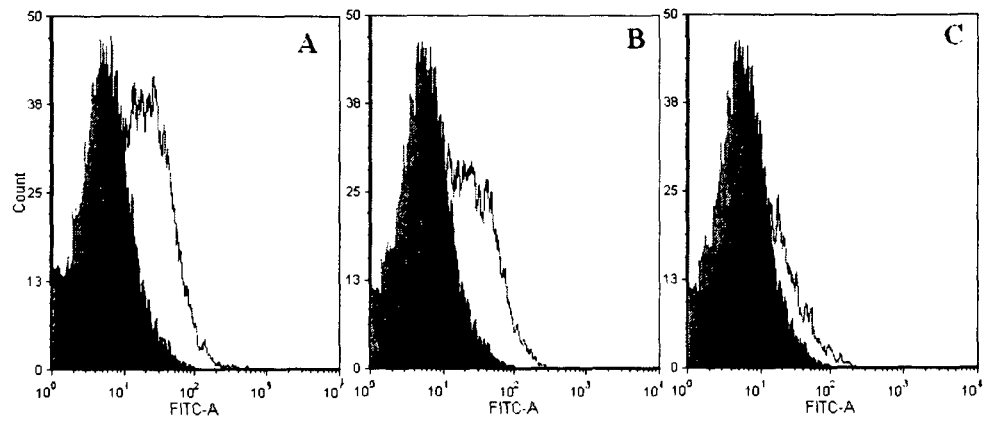

FIG. 11 depicts the FACS profile for transfection of mbm-DCs with lipoplexes of 1(A), 2(B) & 3(C) and p-α5GFP plasmid DNA.

Figure 12:
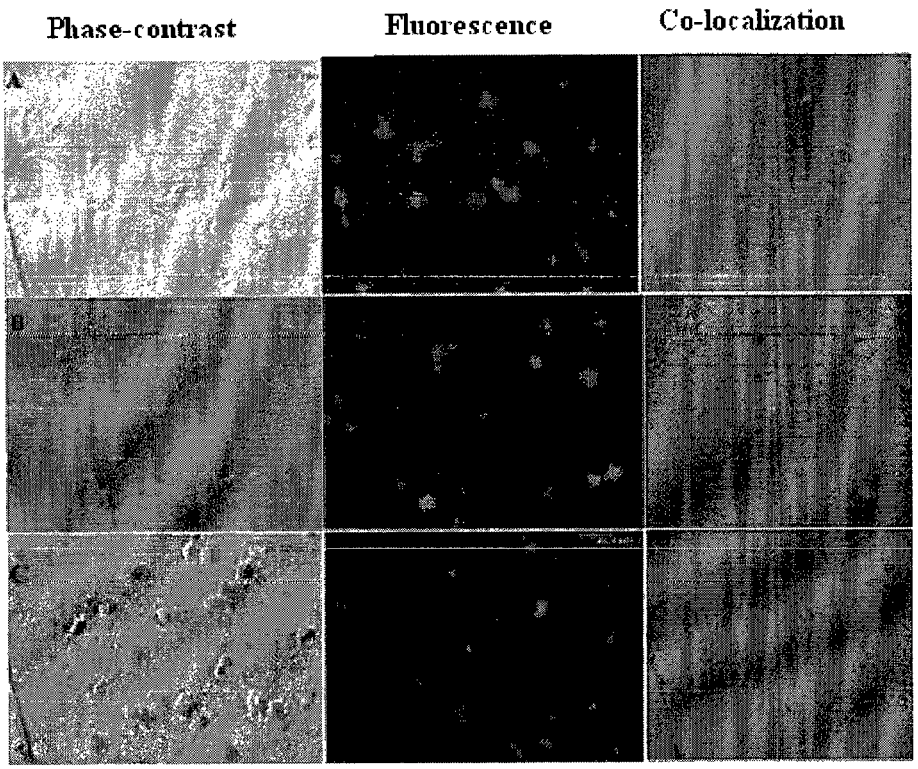

FIG. 12 depicts GFP expression in mbm DCs transfected with liposomal formulations of the cationic amphiphiles 1 (A), 2 (B) & 3 (C) with pα5GFP plasmid. Bar=2 micron; Magnification: 40×.

Figure 13:
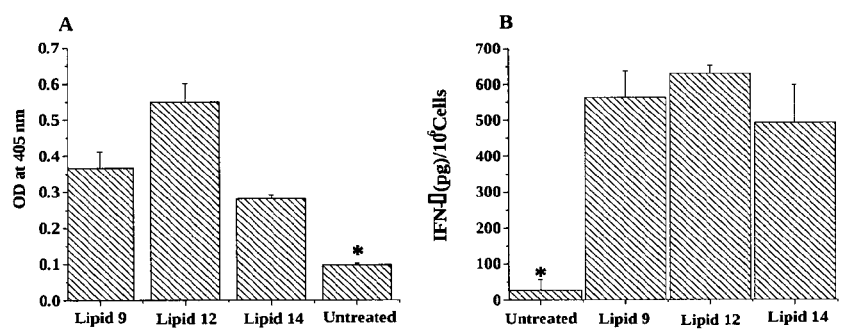

FIG. 13 summarizes humoral and cellular immune responses in C57BL/6J mice upon subcutaneous administration of mbmDCs pre-transfected with lipoplexes of 1, 2 & 3 and p-CMV-β-gal as a model genetic vaccine. A) 6-8 weeks old female C57BL/6 mice (each weighing 20-22 g, n=4) were immunized subcutaneously with 5×10$^5$ cells of pre-transfected mbmDCs (twice with a seven-day interval). Two weeks after the second immunization, serum samples were collected from mice and assayed for β-gal antibodies by ELISA. The Y-axis represents absorbance obtained with a 1:200 dilution of serum (*P<0.005 for cationic amphiphiles 1, 2 & 3 compared with values for untreated mbmDCs). B) Two weeks after the second immunization, splenocytes were collected and used immediately (without in vitro restimulation) for T-cell (cellular) responses by ELISA (*P<0.005 for the cationic amphiphiles 1, 2 & 3 compared with values for untreated mbmDCs).

DETAILED DESCRIPTION OF THE INVENTION

Mannose receptor is a 180 kDa transmembrane protein consisting of five domains: a cystine rich amino terminus, a fibronectin type II repeat region, eight carbohydrate recognition domains (CRD), a transmembrane domain and a cytoplasmic domain. The mannose receptor selectively binds to molecules or micro-organisms carrying sugars such as mannose, fucose, N-acetylglucosamine and glucose on their surface through the eight CRD domains (Apostolopoulos, V. et al. Curr. Mol. Med. 2001; 1:469-474). A major contribution to the binding is provided by the extensive network of hydrogen bonds and coordination bonds between two equatorial, vicinal hydroxyl groups (at positions 3 & 4) in D-mannose, a calcium ion, two asparagines and two glutamic acid residue of the receptor protein (Weis, W. I. et al. Nature 1992; 360: 127-134, Drickamer, K. Nature 1992; 360:183-186). Thus, the mannose receptor plays a key role in imparting protective immunity against a host of antigenic micro-organisms expressing mannose on their cell wall. Since both dendritic cells and macrophages (antigen presenting cells, APCs) predominantly express endocytic mannose receptors on their cell surfaces (Apostolopoulos, V. et al. Curr. Mol. Med. 2001; 1:469-474), the selective uptake of cationic lipid:DNA complexes (lipoplexes) by the APCs should, in principle, be enhanced by the covalent modification of the liposomal surface with APC specific ligands. This would also prevent the non-specific uptake of lipid:DNA complex by somatic cells such as myocytes or keratinocytes. In other words, if such mannose-receptor specific cationic amphiphiles complexed with genetic material encoding antigens are injected into patients, they are likely to elicit better immune response through enhanced transfection of antigen presenting cells.

The above-mentioned properties of the mannose receptor have been amply exploited in the development of gene delivery reagents capable of targeting the macrophages and dendritic cells (Ferkol, T. et al. Proc. Natl. Acad. Sci. USA 1996; 93:101-105, Diebold, S. S. et al. J. Biol. Chem. 1999; 274: 19087-19094, Kawakami, S. et al. Gene Ther. 2000; 7:292-299). Hashida and co-workers have reported on the potency of mannosylated cationic liposomal formulation in enhancing immune response through the targeted delivery of DNA to APC (Hattori, y. et al. Biochem. Biophys. Res. Comm. 2004; 317:992-999). Grandjean et. al have shown that synthetic lysine based clusters of carbocyclic acids such as quinic and shikimic acid act as effective ligands for the mannose receptor of dendritic cells (Grandjean, C., et al. Chembiochem, 2001; 2:747-757). Most recently, Srinivas, R. et al demonstrated that cationic amphiphiles containing mannose-mimicking quinic acid and shikimic acid head-groups deliver genes to APCs via mannose receptor (Srinivas, R. et al J. Med. Chem. 2010; 317:992-999) To this end, the present invention relates to use of a novel series of cationic amphiphiles containing mannose-mimicking shikimic and quinic acid head-groups (e.g. 1 and 2) for use in transferring genes into dendritic cells, the most professional antigen presenting cells (APCs) as well as for use in genetic immunization. The presently described novel cationic amphiphiles with mannose-mimicking shikimic and quinic acid head-groups (e.g. 1 & 2) are expected to exhibit more systemic stability than their mannosylated counterpart 3 since the hydrolytically more susceptible anomeric bond of mannosylated cationic amphiphile 3 is replaced by hydrolytically more stable amide bond in the molecular architectures of 1 & 2.

The present invention also relates to processes for the preparations of the said novel cationic amphiphiles with mannose-mimicking head-groups as well as the synthetic processes for their mannosyled analog. In addition, the present invention also discloses the mannose receptor mediated gene transfer properties of the presently disclosed cationic amphiphiles in antigen presenting cells (APCs) including cultured antimouse macrophage cells (APC) and mouse dendritic cells (DCs) as well as their transfection properties in cultured mouse fibroblast cells (NIH 3T3, as control non-APCs). The novel cationic amphiphiles containing mannose-mimicking shikimic and quinic acid head-groups are potentially useful to deliver genetic materials encoding therapeutic antigens to antigen presenting cells which over express mannose receptors.

The distinctive novel structural features common to the cationic amphiphiles with mannose-mimicking head-groups disclosed in the present invention include: (1) The presence of hydrophobic groups which are directly linked to the positively charged nitrogen atom and (2) the presence of mannose receptor binding polar quinic acid head-groups covalently linked to the positively charged quaternized nitrogen atoms through a lysine functionality. It is believed that these unique structural features contribute significantly to the mannose receptor mediated gene transfer efficiencies of the glycomimicking cationic amphiphiles disclosed herein. The area of science that is likely to be benefited most from the present invention is the field of genetic immunization or DNA vaccination. "cationic" means the positive charge is either on quaternized nitrogen or on a protonated nitrogen atom. The cationic characters of the present amphiphiles may contribute to the enhanced interaction of the amphiphiles with biologically active molecules such as nucleic acids and/or with cell constituents such as plasma membrane glycoproteins. Such enhanced interaction between the cationic amphiphiles and therapeutically active biological macromolecules and/or cell membrane constituents may play a key role in successfully transporting the therapeutic molecules into the cells.

The cationic glycomimicking lipids of the present invention have certain common structural and functional groups. As such, the said cationic amphiphiles may be represented by the following generic formula (A):

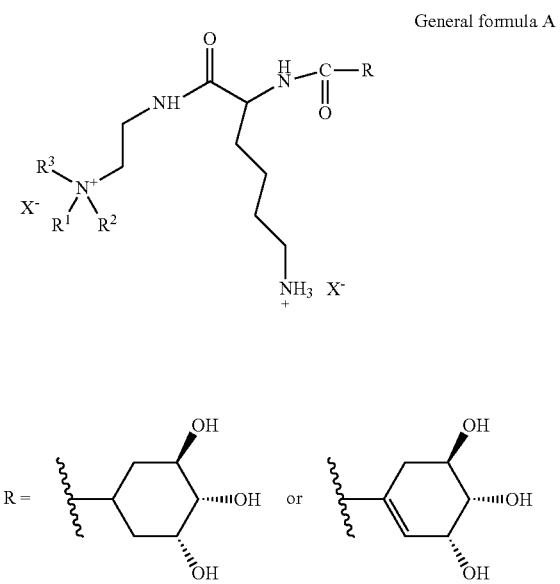

General formula A

Wherein each of $R^1$ and $R^2$ is independently hydrogen or a lipophilic moiety containing at least eight carbon atoms and is optionally selected from 8-24 carbon containing alkyl, mono-, di- and tri-unsaturated alkenyl ($C_8$-$C_{22}$) provided both $R^1$ and $R^2$ are not hydrogen;

$R^3$ is independently hydrogen or alkyl ($C_1$-$C_5$, straight or branched) or hydroxy or amino-alkyl functional groups ($C_1$-$C_5$, straight or branched);

X is optionally selected from chlorine or bromine atom.

In a preferred embodiment of the present invention, the disclosed cationic lipid is cationic amphiphile 1 wherein $R_1=R_2=$n-hexadecyl, $R_3=$methyl and $X^-$ is a chloride ion the amphiphile no. 1 and shikimic acid is the mannose-mimicking head-group. In another second preferred embodiment of the present invention, the disclosed cationic lipid is cationic amphiphile 2 wherein $R_1=R_2=$n-hexadecyl, $R_3=$methyl and $X^-$ is a chloride ion and quinic acid is the mannose-mimicking head-group. The cationic amphiphiles of the present invention have a lipophilic domain that facilitates the formation of lipid complexes or aggregates in aqueous solutions. The lipophilicity of the hydrophobic domains and the hydrophilicity of the polar quinic acid head-group domains are such that when the cationic lipids are confronted with aqueous solutions, lipid aggregates are formed in the presence or absence of a second compound. Exemplary lipophilic $R_1$ and $R_2$ groups include (1) saturated $C_8$-$C_{22}$ alkyl groups and (2) unsaturated $C_8$-$C_{22}$ alkenyl groups containing 1, 2, or 3 double bonds.

Synthetic strategies employed for preparing the presently described cationic amphiphiles with mannose-mimicking shikimic acid head-groups (X) are depicted below schematically in Schemes 1. Cationic amphiphiles with Shikimic acid head-groups (X, Scheme 1) were synthesized by peptide coupling of the starting mixed tertiary-primary amine shown in Scheme 1 (prepared by reacting N,N-di-n-tetradecylamine with N-tert-butyloxycarbonyl protected 2-bromoethylamine in ethyl acetate in presence of anhydrous potassium carbonate followed by deprotection and neutralization as reported earlier by Kumar, V. V. et al. in Gene. Ther. 2003; 10:1206-1215) with appropriately protected lysine derivative (containing protected side-chain and protected alpha-amine groups). The coupled product (intermediate I, Scheme 1) was deprotected and the resulting amino compound (intermediate II, Scheme 1) upon peptide coupling with tri-O-acetyl shikimic acid derivative afforded the intermediate III (Scheme 1). The intermediate III upon quaternization with huge excess of methyl iodide provided the quaternized intermediate IV (Scheme 1) which upon reaction with methanolic sodium methoxide followed by chloride ion exchange over Amberlyst A-26 Chloride ion exchange resin afforded the target cationic amphiphiles X (Scheme 1). Details of synthetic procedures for cationic amphiphiles X with shikimic acid head-groups are described below in Example 1 for synthesis of cationic amphiphile 1 (as a representative example). Same synthetic strategies were employed for preparing cationic amphiphiles with mannose-mimicking quinic acid head-groups (Y, Scheme 2) as were adopted for syntheses of cationic amphiphiles X with shikimic acid head-groups (Scheme 1) except using O-tetraaceyl derivative of quinic acid instead of using tri-O-acetyl derivative of shikimic acids. The details of synthetic procedures for cationic amphiphiles Y with quinic acid head-groups are described below in Example 2 for synthesis of cationic amphiphile 2 (as a representative example). Synthetic routes followed in preparing the mannosyl analog (3) of the presently described cationic amphiphiles are shown schematically in Scheme 3 and the synthetic details for the preparation of the cationic amphiphile 3 are provided below in Example 3. Structures of all the synthetic intermediates and target cationic amphiphiles shown in Schemes 1-3 were confirmed by $^1$H NMR and FAB mass spectroscopy and the purities of all the target cationic amphiphiles were confirmed by reverse phase analytical HPLC using two different mobile phases. The terms "cationic amphiphiles" and "lipids" have been used interchangeably in the description and claims.

Formulations

The present invention also provides novel formulation comprising optimal amounts of cationic amphiphiles with mannose-mimicking head-groups disclosed herein, nucleic acids and the co-lipids. One or more additional physiologically acceptable substances may be included in the pharmaceutical formulation of the invention to stabilize the formulation for storage or to facilitate successful intracellular delivery of the biologically active molecules. Co-lipids according to the practice of the present invention are useful in mixing with one or more of the glycomimicking amphiphiles. Cholesterol is an excellent co-lipid for use in combination with the presently described amphiphiles to facilitate successful delivery of the biologically active molecules in general and DNA vaccines in particular to APCs. A preferred range of molar ratio of the cationic amphiphile to co-lipid is 1:1. As such, it is within the art to vary the said range to a considerably wide extent. Typically, liposomes were prepared by dissolving the cationic amphiphiles and the co-lipid (Cholesterol or DOPE) in the appropriate mole ratio in a mixture of methanol and chloroform in a glass vial. The solvent was removed with a thin flow of moisture free nitrogen gas and the dried lipid film was then kept under high vacuum for 8 h. The dried lipid film was hydrated in sterile deionized water in a total volume of 1 mL at cationic lipid concentration of 1 mM for a minimum of 12 h. Liposomes were vortexed for 1-2 minutes to remove any adhering lipid film and sonicated in a bath sonicator (ULTRAsonik 28x) for 2-3 minutes at room temperature to produce multilamellar vesicles (MLV). MLVs were then sonicated with a Ti-probe (using a Branson 450 sonifier at 100% duty cycle and 25 W output power) for 1-2 minutes to produce small unilamellar vesicles (SUVs) as indicated by the formation of a clear translucent solution. Biologically active molecules that can be administered intracellularly in therapeutic amounts using the cationic amphiphiles of the present invention include ribosomal RNA, antisense polynucleotide of RNA or DNA, polynucleotide of genomic DNA, cDNA or mRNA that encodes for a therapeutically important antigen or protein. The cationic amphiphiles with mannose-mimicking head-groups disclosed herein may be blended such that one or more of the representatives thereof may be used in a combination to facilitate entry of the said biologically active molecules into cells/tissues.

The cationic amphiphiles disclosed in the present invention may be used either in pure form or in combination with other helper lipids (also known as colipids) such as cholesterol, phosphatidylethanolamine, phosphatidylglycerol, etc. The said therapeutic formulation may be stored at 0-4° C. until complexed with the biologically active therapeutic molecules. Agents that prevent bacterial growth and increase the shelf life may be included along with reagents that stabilize the preparation, e.g., low concentrations of glycerol. It is specifically warned that freezing and thawing cycles could cause loss in efficiency of the formulation.

The formulation of the cationic amphiphiles disclosed herein, co-lipids (cholesterol or DOPE) and the biologically active therapeutic molecules may be administered intravenously besides other routes such as subcutaneous, intramuscular and intraperitonial. Further, the said formulations may be administered to cells at a ratio of 0.1-0.5 microgram of DNA to 50,000 cells in an in vitro system. The amount of cationic amphiphiles could be varied within the cationic amphiphile to DNA charge ratio of 0.3:1 to 9:1 considering two positive charges for one cationic amphiphile and one negative charge of a single nucleotide base.

The invention further provides a process for the preparation of the said formulation comprising the steps of preparing a dispersion of the cationic amphiphiles disclosed in the present invention; contacting said dispersion with a biologically active molecule to form a complex between the said cationic amphiphiles and the said biologically active molecules and contacting the cells with the said complex thereby facilitating transfer of said biologically active molecules into the cells. The present invention also provides with various formulations that facilitate intracellular delivery of biologically active molecules.

Transfection of Antigen Presenting Cells (APCs) Via Mannose Receptors:

The relative in vitro gene delivery of lipids 1-3 were first evaluated in RAW 264.7 cells (murine macrophage cell, an antigen presenting cell) across the lipid:DNA charge ratios 8:1 to 1:1 using DOPE as a co-lipid and luciferase as the reporter gene in the conventional reporter gene expression assay. The cationic amphiphiles containing a mono shikimic acid and mono quinic acid head-groups showed higher in vitro transfection efficiencies than their control mannosylated lipid 3 across the lipid:DNA charge ratios 2:1-8:1 (FIG. 4). The transfection efficiencies of the lipids 1 & 2 as well as those of mannosyl analog 3 were enhanced further when DOPC was used as a co lipid compared to using DOPE as a co lipid at 8:1 ratio (FIG. 5). Such improved transfection efficiencies with DOPC is likely to provide enhanced antigen expression in bone marrow derived hard-to-transfect mouse APCs.

The mannose receptor specificities of the presently described cationic amphiphiles. Toward evaluating the mannose receptor selective transfection properties of the cationic amphiphiles 1, 2 and 3, the in vitro gene transfer efficiencies of the cationic amphiphiles were first evaluated in RAW 264.7 cells (murine macrophage, an antigen presenting cell expressing mannose receptor on its cell surface) in presence and in absence of mannan (a high affinity ligand for mannose receptor) across the lipid:DNA charge ratio 8:1 to 1:1 using DOPE as a co lipid. The transfection efficiencies were found to be significantly diminished for the lipids 1, 2 and 3 when the RAW cells were pretreated with mannan. But the transfection efficiency of these lipids were not diminished in NIH3T3 cells (murine fibroblast cells which does not express mannose receptor) when the cells were pretreated with mannan (FIGS. 6-8). Similar transfection profiles were also observed in RAW cells as well as in NIH3T3 cells when the cationic amphiphiles 1, 2 and 3 were used in combination with DOPC as a co lipid at lipid:DNA charge ratio of 8:1 (FIG. 9). Thus, the findings summarized in FIGS. 6-9 convincingly demonstrated that the cationic amphiphiles 1 and 2 containing mannose-mimicking shikimic and quinic acid head-groups, respectively, as well as their mannosyl counterpart (3) deliver genes to APCs via mannose receptor. Among the various APCs, DCs are the most potent antigen presenting cells, capable of effective antigen presentation to naïve T cells (Romini N, et al. J Exp Med. 1994; 180:83-93). In the field of DNA vaccination, transfected DCs are the key players for efficient cytotoxic T-lyphocyte (CTL) responses (Denis-Mize K S, et al. Gene Ther. 2000; 24:2105-112, Condon C, et al. Nat Med. 1996; 10: 1122-1128, Akbari O, et al. J Exp Med. 1999; 189:169-178, Coombes B. K. et al. Immunol Lett. 2001; 78:103-111, Porgador A, et al. J Exp Med. 1998; 188:1075-1082, Timares L, et al. J Immunol. 2003; 170:5483-5490, Sbai H, et al. Vaccine. 2002; 20:3137-3147, Irvine A S, et al. Nat Biotechnol. 2000; 18: 1273-1278). For a successful DNA vaccination and antigen presentation by DCs, DNA internalization or DNA loaded DCs are not sufficient. The antigen encoded DNA vaccine needs to be delivered to the nucleus of the dendritic cell in order to express the respective antigen. Then the antigens are processed and displayed on MHC class I and class II molecules of activated DCs (Samantha J, et al. Advanced Drug Delivery Reviews 2005; 57:377-390). Effective transfection to DCs is restricted by the lysosomal or phagosomal degradation of the internalized DNA before its transportation to nucleus. This is why DCs are hard-to-transfect. The transfection rates differ greatly from one group to other with the transfection efficiencies ranging from 0-10% (Alijagic S, et al. Eur J Immunol. 1995; 25:3100-3107, Arthur J. F. et al. Cancer Gene Ther. 1997; 1:17-25, Lohmann S, et al. Cancer Gene Ther. 2000; 4:605-14, Strobel I, et al. Gene Ther. 2000; 23:2028-35). The mannose receptor (MR) expressed on the surface of immature DCs are involved in endocytosis and phagocytosis (Ezekowitz, R A B, et al. J. Exp. Med. 1990; 172:1785-1794). First, the transfection efficiency of the cationic amphiphiles 1, 2 & 3 were evaluated in mouse bone marrow derived dendritic cells. To this end, the immature dendritic cells were isolated from the bone marrow of C57BL/6J mice by culturing with GM-CSF and IL-4 following a previously described protocol (Inaba K, et al. J Exp Med 1992; 176:1693-1702). First, the presence of various DC markers in the isolated mbm DCs were confirmed by fluorocytometric analysis. The freshly isolated mbm DCs were treated with FITC/PE conjugated monoclonal antibodies for various DC markers and their FACS profiles monitored. Findings in flow cytometry confirmed the characteristics of immature DCs having high intracellular levels of MHC class II molecules, low CD 86, high levels of CD11c, CD 40 and mannose receptor (FIG. 10).

After confirming the presence of expected DC markers on the surface of the isolated DCs (FIG. 10), the transfection efficiencies of the cationic amphiphiles 1, 2 & 3 were evaluated in mbmDCs. To evaluate the transfection efficiency of the lipids 1, 2 & 3 in mbm DCs, the freshly isolated DCs were transfected with complexes of cationic liposomes of lipids 1, 2 & 3 and pα5GFP plasmid (plasmid DNA encoding green fluorescent protein). Importantly, the FASC analysis for the expression of GFP in dendritic cells revealed enhanced DC transfection efficiencies (up to 9%) for the lipids 1 and 2 (FIG. 11) compared to the transfection efficiency of their control mannosyl analog 3 (5%). The fluorescence microscopic pictures for mbm DCs transfected with the complexes of the cationic liposomes of lipids 1, 2 & 3 and pα5GFP are shown in FIG. 12. Thus, the efficiencies of the presently described cationic amphiphiles with mannose-mimicking shikimic and quinic acid head-groups in transfecting dendritic cells is remarkably higher (by ~3 fold) than those of the recently reported first generation cationic amphiphiles containing mannose-mimicking shikimic acid head-group (Srinivas, R. et al. J. Med. Chem. 2010; 53:1387-1391).

Humoral Immune Response Upon Intramuscular Genetic Immunization in Mice:

The therapeutic potential of the presently described glyco-mimicking cationic amphiphiles as DNA vaccine carriers were evaluated by intramuscularly immunizing Balb/c mice with lipoplexes of lipids 1-3 in complexation with 25 μg of pCMV-SPORT-β-gal (as a model antigen encoded DNA) at lipid:DNA charge ratio of 6:1. Three weeks post primary immunization, a booster dose of lipoplexes having the same amount of DNA as in the first dose was administered and the mice were bled two week after the administration of this second booster, dose. Antibodies generated against the plasmid encoded β-galactosidase protein (the model antigen) was measured by the ELISA assay. As depicted in FIG. 13, mice immunized with lipoplexes of lipids 1-3 exhibited two fold higher antibody titers than the mice injected with same amount of naked DNA.

Applications:

The process of the present invention can be exploited for preparing cationic amphiphiles with mannose-mimicking cationic amphiphiles and for delivering biologically active compounds such as DNA, RNA, proteins, etc. into antigen presenting cells in genetic immunization. The present inventions are particularly useful for mannose receptor specific delivery of polyanions, polypeptides or nucleopolymers into the antigen presenting cells. The present invention is directed to methods of eliciting immune responses in animals through administering complexes of liposomes prepared with presently described cationic amphiphiles and a polynucleotide coding for an antigentic determinant. Furthermore, the present invention is also directed to methods of eliciting active immunity against an infectious disease in animals through administering complexes of the presently described cationic amphiphiles and a polynucleotide coding for the infectious disease causing protein. The present invention is also related to the genetic immunization methods wherein the polynucleotide is an expression vector comprising a DNA sequence encoding the antigenic determinant of the infectious disease causing immunogen and wherein the transcription of the DNA is under the control of a promoter. The present invention, is further directed to a genetic immunization wherein the polynucleotide is an RNA molecule encoding for an infectious immunogen. In particular, the presently disclosed novel cationic amphiphiles with mannose-mimicking shikimic and quinic acid head-groups hold potential for future exploitation in genetic immunization in delivering DNA or RNA encoding infectious immunogen. The most distinguishing feature of the present invention is that the efficiencies of the novel cationic amphiphiles disclosed herein in transfecting dendritic cells, the most professional antigen presenting cells, is ~4 fold superior to those of the first generation cationic amphiphiles with shikimic and quinic acid head-groups recently disclosed by Srinivas, R. et al. J. Med. Chem. 2010; 53:1387-1391.

The following examples are given by way of illustration of the present invention and therefore should not be construed to limit the scope of the present invention.

EXAMPLE 1

Synthesis of the Cationic Amphiphile (1) (Scheme 1, X, n=13).

Step (i): Solid HOBt (0.28 g, 2 mmol) and EDCI (0.4 g, 2 mmol) were added sequentially to an ice cold and stirred solution of $N^\alpha$—Z—$N^\epsilon$—BOC-L-Lysine (0.76 g, 2 mmol) in 5 mL dry DCM/dry DMF (9:1, v/v) under nitrogen atmosphere. After half an hour, N-2-aminoethyl-N,N-di-n-hexadecylamine (0.8 g, 1.5 mmol) dissolved in 5 mL dry DCM was added to the reaction mixture. The resulting solution was left stirred at 25° C. for 12 h, diluted with excess DCM and washed sequentially with saturated sodium bicarbonate (~2×50 mL) and water (~2×50 mL). The organic layer was dried over anhydrous sodium sulfate, filtered and the solvent from the filtrate removed by rotary evaporation. The residue upon column chromatographic purification with 60-120 mesh silica gel using 1-1.5% methanol in dichloromethane (v/v) as eluent afforded 1.1 g (80% yield) of the pure intermediate I. ($R_f$=0.5, 5% methanol in dichloromethane, v/v).

$^1$H NMR (300 MHz, CDCl$_3$): δ/ppm=0.9 [t, 6H, CH$_3$—(CH$_2$)$_{13}$—]; 1.2-1.9 [m, 54H, —CH$_2$(CH$_2$)$_{13}$—; 9H, CO—O—C(CH$_3$)$_3$; 6H, LysC$^\gamma$H$_2$, LysC$^\delta$H$_2$, LysC$^\beta$H$_2$]; 2.4-2.7 [m, 4H, —N(—CH—CH$_2$—)$_2$; 2H, —N—CH$_2$—CH$_2$—NH—CO] 3.0-3.1 [m, 2H, LysC$^\omega$H$_2$]; 3.3-3.4 [m, 2H, —N—CH$_2$—CH$_2$—NH—CO]; 4.0 [m, 1H, BOC—NH]; 4.5 [m, 1H, LysC$^\alpha$H]; 5.0 [d, 2H, —O—CH$_2$—C$_6$H$_5$]; 5.5 [m, 1H, —NH—Z]; 7.2-7.5 [m, 5H, O—CH$_2$—C$_6$H$_5$].

Step (ii): The intermediate I prepared in above step (1.1 g, 1.2 mmol) was dissolved in 8 mL methanol and 100 μL 2N hydrochloric acid. Pd(OH)$_2$/C (0.3 g) was added to the reaction mixture and air was removed. The resultant reaction mixture was stirred at 25° C. for 14 h under hydrogen atmosphere (2 atmos). The reaction mixture was filtered using celite and the filtrate was dried over anhydrous sodium sulphate and the solvent from the filtrate removed by rotary evaporation afforded the 0.9 g (90% yield) of the crude amine intermediate II. ($R_f$=~0.4, 10% methanol-chloroform, v/v). This crude amine intermediate was not purified further and was used directly in step (iii) below.

Step (iii) Solid HOBt (0.1 g, 1.4 mmol) and EDCI (0.15 g, 1.4 mmol) were added sequentially to an ice cold and stirred solution of 3,4,5-Triacetoxycyclohex-1-ene carboxylic acid (0:23 g, 1.4 mmol) in 5 mL dry DCM/dry DMF, (9:1, v/v). After half an hour, the intermediate II prepared in above step (0.4 g, 0.54 mmol) was dissolved in 4 mL dry DCM (neutralized with 0.4 mL of tri ethylene amine) was added to the reaction mixture. The resulting solution was left stirred at 25° C. for 12 h, diluted with excess DCM and washed sequentially with saturated sodium bicarbonate (~2×40 mL) and water (~2×40 mL). The organic layer was dried over anhydrous sodium sulfate, filtered and the solvent from the filtrate removed by rotary evaporation. The residue upon column chromatographic purification with 60-120 mesh silica gel using 1.5-2% methanol in dichloromethane (v/v) as eluent afforded 0.4 g (72% yield) of the pure intermediate III. ($R_f$=0.5, 5% methanol in dichloromethane, v/v).

$^1$H NMR (300 MHz, CDCl$_3$): δ/ppm=0.9 [t, 6H, CH$_3$—(CH$_2$)$_{13}$—]; 1.2-1.5 [m, 54H, 2×-CH$_2$(CH$_2$)$_{13}$—; 9H, CO—O—C(CH$_3$)$_3$]; 1.6-1.9 [m, 6H, LysC$^\gamma$H$_2$, LysC$^\delta$H$_2$, LysC$^\beta$H$_2$]; 2.0-2.1 [3s, 9H, 3×-COCH$_3$]; 2.2-2.4 [dd, 2H, shik6-H,H']; 2.7-3.2 [m, 4H, —N(—CH—CH$_2$—)$_2$; 2H, —N—CH$_2$—CH$_2$—NH—CO; 2H, LysC$^\omega$H$_2$]; 3.4-3.5 [m, 2H, —N—CH$_2$—CH$_2$—NH—CO]; 4.3-4.4 [m, 1H, LysC$^\alpha$H]; 4.7 [m, 1H, BOC—NH]; 5.1-5.3 [m, 2H, shik-4-H, shik-5-H]; 5.6-5.7 [m, 1H, shik-3-H]; 6.4 [d, 1H, shik-2-H]; 7.1 [m, 1H, CO—NH].

ES-MS: m/z=1020 [M+1]$^+$ for C$_{58}$H$_{106}$N$_4$O$_{10}$.

Step (iv): The intermediate III prepared in above step (0.4 g, 0.4 mmol) was dissolved in 2 mL chloroform/methanol (1:1, v/v) and 5 mL methyl iodide was added to the solution. The reaction mixture was stirred at room temperature for 6 h and the solvent was removed on a rotary evaporator. The residue upon column chromatographic purification with silica gel (60-120 mesh size) and 2-2.5% methanol in dichloromethane (v/v) as eluent afforded 0.35 g (82% yield) of pure intermediate IV. ($R_f$=0.45, 5% methanol in dichloromethane, v/v).

$^1$H NMR (300 MHz, CDCl$_3$): δ/ppm=0.9 [t, 6H, CH$_3$—(CH$_2$)$_{13}$—]; 1.2-1.6 [m, 52H, 2× —(CH$_2$)$_{13}$—, 4H, LysC$^\gamma$H$_2$, 9H, CO—O—C(CH$_3$)$_3$]; 1.65-2.0 [m, 4H, —N$^+$(—CH$_2$—CH$_2$—)$_2$, 4H, LysC$^\delta$H$_2$, LysC$^\beta$H$_2$]; 2.0-2.15 [3s, 9H, 3×-COCH$_3$]; 2.3-2.5 [dd, 1H, shik6-H,H']; 3.0-3.1 [m, 2H, LysC$^\omega$H$_2$]; 3.3 [s, 3H, —N$^+$CH$_3$]; 3.4-3.5 [m, 4H, —N$^+$(—CH$_2$—CH$_2$—)$_2$]; 3.7-3.8 [m, 4H, —N$^+$—CH$_2$—CH$_2$—NH—CO]; 4.4 [m, 1H, LysC$^\alpha$H]; 4.8 [m, 1H, BOC—NH] 5.1-5.3 [m, 2H, shik-4-H, shik-5-H]; 5.7 [t, 1H, shik-3-H]; 6.5-6.6 [d, 1H, shik-2-H].

ES-MS: m/z=1034 [M]$^+$ for C$_{59}$H$_{109}$N$_4$O$_{10}$.

Step (v): The intermediate IV prepared above step (0.35 g, 0.33 mmol) was dissolved in 2 mL methanol and $K_2CO_3$ (0.2 g, 1.5 mmol) was added to the reaction mixture to increase the pH~9. The reaction mixture was allowed to stir at 25° C. for 30 min, neutralized with Amberlite IR120 ($H^+$), filtered and the filtrate was dried over anhydrous sodium sulphate and concentrated on a rotary evaporator afforded 0.25 g (80% yield) of the intermediate V. ($R_f$=~0.6, 20% methanol-chloroform, v/v).

Step (vi): To the ice cold solution of the intermediate V prepared in above step (0.25 g, 0.27 mmol) dissolved in. 2 mL dry DCM. 0.6 ml of TFA (trifluoroacetic acid) added and the mixture was allowed to stir for 3-4 h. TFA was removed by applying nitrogen, followed by the chloride ion exchange chromatography (using amberlyst A-26 chloride ion exchange resin). The final compound was recrystallized using MeOH & Acetone afforded 0.15 g (67% yield) of the pure target compound 1 as a white solid. ($R_f$=~0.3, 10% methanol-chloroform, v/v).

$^1$H NMR: (600 MHz, $CD_3OD+CDCl_3$): δ/ppm=0.9 [t, 6H, $2 \times CH_3—(CH_2)_{13}—$]; 1.2-1.5 [m, 52H, $2 \times -CH_2(CH_2)_{13}-$]; 1.6-2.0 [m, 6H, $LysC^\gamma H_2$, $LysC^\delta H_2$, $LysC^\beta H_2$, 4H, $—N^+(—CH_2—CH_2—)_2,2H_,$]; 2.2 [dd, 1H, shik6-H]; 2.8 [dd, 1H, shik-6-H']; 2.9-3.2 [m, 2H, $LysC^\omega H_2$, 4H, $—N^+(—CH_2—CH_2—)_2$]; 3.3-3.5 [m, 3H, $—N^+CH_3$; 2H, $—N^+—CH_2—CH_2—NH—CO$]; 3.5-3.7 [m, 1H, shik-4-H, 2H, $—N^+—CH_2—CH_2—NH—CO$]; 4.0-4.1 [m, 1H, shik-5-H]; 4.3-4.5 [m, 1H, $LysC^\alpha H$, 1H, shik3-H]; 6.5 [s, 1H, shik2-H].

ES-MS: m/z=808 [M]$^+$ for $C_{48}H_{96}N_4O_5$.

EXAMPLE 2

Synthesis of the Cationic Amphiphile (2) (Scheme 2, X, n=13)

Step (i): Solid HOBt (0.09 g, 0.67 mmol) and EDCI (0.13 g, 0.67 mmol) were added sequentially to an ice cold and stirred solution of 1,3,4,5-Tetraacetoxycyclohexane carboxylic acid (0.24 g, 0.67 mmol) in 5 mL dry DCM/dry DMF (9:1, v/v) under nitrogen atmosphere. After half an hour, the intermediate II as prepared in scheme 1 (0.38 g, 0.51 mmol) was dissolved in dry DCM was added to the reaction mixture. The resulting solution was left stirred at 25° C. for 12 h, diluted with excess DCM and washed sequentially with saturated sodium bicarbonate (~3×50 mL) and water (~3×50 mL). The organic layer was dried over anhydrous sodium sulfate, filtered and the solvent from the filtrate removed by rotary evaporation. The residue upon column chromatographic purification with 60-120 mesh silica gel using 1.5-2% methanol in dichloromethane (v/v) as eluent afforded 0.31 g (56% yield) of the pure intermediate I. ($R_f$=0.5, 5% methanol in dichloromethane, v/v).

$^1$H NMR (300 MHz, $CDCl_3$): δ/ppm=0.9 [t, 6H, $2 \times CH_3—(CH_2)_{13}—$]; 1.2-1.7 [m, 56H, $2 \times —CH_2(CH_2)_{13}—$; 9H, $CO—O—C(CH_3)_3$; 4H, $LysC^\gamma H_2$, $LysC^\delta H_2$]; 1.8-2.2 [m, 2H, $LysC^\beta H_2$; 12H, $4 \times CH_3$]; 2.3-2.8 [m, 4H, qui6-H,H', qui2-H, H', 4H, $—N(—CH_3—CH_2—)_2$, 2H, $—N—CH_2—CH_2—NHCO$]; 3.0-3.3 [m, 2H, $LysC^\omega H_2$, 2H, $—N—CH_2—CH_2—NH—CO$]; 4.4 [m, 1H, $LysC^\alpha H$]; 4.7 [m, 1H, BOC—NH]]; 4.9-5.1 [dd, 1H, qui-4-H]; 5.3-5.45 [ddd, 1H, qui5-H]; 5.5-5.6 [m, 1H, qui3-H].

ES-MS: m/z: 1080 [M+1]$^+$ for $C_{60}H_{110}N_4O_{12}$

Step (ii): The intermediate I prepared in above step (0.3 g, 0.29 mmol) was dissolved in 2 mL chloroform/methanol (1:1, v/v) and 5 mL methyl iodide was added to the solution. The reaction mixture was stirred at room temperature for 6 h and the solvent was removed on a rotary evaporator. The residue upon column chromatographic purification with silica gel (60-120 mesh size) and 2-2.5% methanol in dichloromethane (v/v) as eluent afforded 0.18 g (58% yield) of pure intermediate II. ($R_f$=0.45, 5% methanol in dichloromethane, v/v).

$^1$H NMR (300 MHz, $CDCl_3$): δ/ppm=0.9 [t, 6H, $2 \times CH_3—(CH_2)_{13}—$]; 1.2-1.5 [m, 52H, $2 \times —CH_2(CH_2)_{13}—$; 9H, $CO—O—C(CH_3)_3$]; 1.6-1.9 [4H, $—N(—CH_2—CH_2—)_2$; 6H, $LysC^\gamma H_2$, $LysC^\delta H_2$, $LysC^\beta H_2$]; 2.0-2.3 [4s, 12H, $4 \times CH_3$]; 2.4-2.7 [dd, 2H, qui6-H,H'; dd, 2H, qui2-H,H']; 3.1 [d, 2H, $LysC^\omega H_2$]; 3.2 [s, 3H, $N^+CH_3$]; 3.3-3.4 [m, 4H, $—N^+(—CH_2—CH_2—)_2$]; 3.6-3.8 [m, 4H, $—N^+—CH_2—CH_2—NHCO$]; 4.3-4.4 [m, 1H, $LysC^+H$]; 4.9-5.1 [m, 1H, BOC—NH; 1H, qui4-H]; 5.3-5.45 [ddd, 1H, qui5-H]; 5.5-5.6 [d, 1H, qui3-H].

ES-MS: m/z: 1094 [M]$^+$ for $C_{61}H_{113}N_4O_{12}$.

Step (iii): The intermediate II prepared above step (0.18 g, 0.2 mmol) was dissolved in 2 mL methanol and $K_2CO_3$ (0.1 g, 1.5 mmol) was added to the reaction mixture to increase the pH~9. The reaction mixture was allowed to stir at 25° C. for 30 mins, neutralized with Amberlite IR120 ($H^+$), filtered and the filtrate was dried over anhydrous sodium sulphate. The solvent was removed by rotary evaporator afforded 0.11 g (72% yield) of the intermediate III. ($R_f$=~0.6, 20% methanol-chloroform, v/v).

Step (iv) & (v): To the ice cold solution of the intermediate III prepared in above step (0.1 g, 0.06 mmol) was dissolved in 2 mL dry DCM, 0.6 ml of TFA (trifluoroacetic acid) added and the mixture was allowed to stir for 3-4 h. TFA was removed by applying nitrogen, followed by chloride ion exchange chromatography (using amberlyst A-26 chloride ion exchange resin). The final compound was recrystallized using MeOH &Acetone afforded 0.08 g (75% yield) of the pure target compound 2 as a white solid. ($R_f$=~0.3, 10% methanol-chloroform, v/v).

$^1$H NMR: (600 MHz, $CD_3OD+CDCl_3$): δ/ppm=0.9 [t, 6H, $CH_3—(CH_2)_{13}—$]; 1.2-1.5 [m, 52H, $\{—CH_2(CH_2)_{13}—\}_2$; 2H, $LysC^\delta H_2$]; 1.65-2.2 [m, 4H, $—N^+(—CH_2—CH_2—)_2$; 2H, $LysC^\beta H_2$, $LysC^\gamma H_2$; 2H, qui6-H,H'; 2H, qui2-H,H']; 2.9-3.7 [m, 4H, $—N^+(—CH_2—CH_2—)_2$; 3H, $—N^+CH_3$; 2H, $LysC^\omega H_2$; 4H, $—N^+—CH_2—CH_2—NH—CO$; 1H, qui4-H]; 4.0-4.2 [m, 2H, qui-3H, qui-5H]; 4.4 [m, 1H, $LysC^\alpha H$].

ES-MS: m/z: 826 [M]$^+$ for $C_{48}H_{97}N_4O_6$.

EXAMPLE 3

Synthesis of Control Mannosylated Lipid (3) (Scheme 3):

Step (i): Solid HOBt (0.36 g, 2.3 mmol) and EDCI (0.45 g, 2.3 mmol) were added sequentially to an ice cold and stirred solution of 2-(tert-butyldiphenylsilyloxy)acetic acid (0.74 g, 2.3 mmol, a, scheme 3) in 5 mL dry DCM/thy DMF (9:1, v/v) under nitrogen atmosphere. After half an hour, intermediate N-2-[(N$^\epsilon$—Z-L-Lysyl)]aminoethyl-N,N-di-n-hexadecylamine (1.2 g, 1.5 mmol, prepared as described in Pramanik, D. et al. J Med Chem. 2008; 51:7298-7302) was dissolved in dry DCM was added to the reaction mixture. The resulting solution was left stirred at 25° C. for 12 h, diluted with excess chloroform and washed sequentially with saturated sodium bicarbonate (~3×50 mL) and water (~3×50 mL). The organic layer was dried over anhydrous sodium sulfate, filtered and the solvent from the filtrate removed by rotary evaporation. The residue upon column chromatographic purification with 60-120 mesh silica gel using 1-1.5% methanol in chloroform (v/v) as eluent afforded 1.6 g (73% yield) of the pure intermediate I. ($R_f$=0.5, 5% methanol in dichloromethane, v/v).

$^1$H NMR (300 MHz, $CDCl_3$): δ/ppm=0.9 [t, 6H, $2 \times CH_3—(CH_2)_{13}—$]; 1.0-1.1 [m, 9H, $—C(CH_3)_3$]; 1.2-1.5 [m, 52H, $2 \times -(CH_2)_{13}$; 4H, $—N(—CH_2—CH_2—)_2$; 4H, $LysC^\gamma H_2$, $LysC^\delta H_2$]; 1.8-1.9 [m, 2H, $LysC^\beta H_2$]; 2.4-2.5 [t, 4H, —N(—CH$_2$—CH$_2$—)$_2$]; 2.5-2.6 [t, 2H, —N—CH$_2$—CH$_2$—NH—CO]; 3.0-3.2 [m, 2H, LysC$^\omega$H$_2$]; 3.25-3.4 [m, 2H, —N—CH$_2$—CH$_2$—NH—CO]; 4.0-4.1 [s, 2H, —CH$_2$—O—Si—]; 4.3-4.4 [m, 1H, LysC$^\alpha$H]; 4.9-5.0 [m, —CH$_2$—C$_6$H$_5$; —CH$_2$—O—Si—]; 7.2-7.7 [m, 15H, —(C$_6$H$_5$)$_3$.

ES-MS: m/z: 1069 [M+2]$^+$ for C$_{66}$H$_{110}$N$_4$O$_5$Si.

Step (ii): The intermediate I prepared in above step (1.2 g, 1.5 mmol) was dissolved in dry THF and tertiary butyl ammonium fluoride (0.6 g, 2.3 mmol) was slowly added at 0° C. The resultant solution left stirred at 25° C. for 2 h, diluted with excess chloroform and washed sequentially with saturated sodium bicarbonate (~3×50 mL) and water (~3×50 mL). The organic layer was dried over anhydrous sodium sulfate, filtered and the solvent from the filtrate removed by rotary evaporation. The residue upon column chromatographic purification with 60-120 mesh silica gel using 1.5-2% methanol in chloroform (v/v) as eluent afforded 1 g (80% yield) of the pure intermediate II. (R$_f$=0.3, 5% methanol in chloroform, v/v).

$^1$H NMR (300 MHz, CDCl$_3$): δ/ppm=0.9 [t, 6H, CH$_3$—(CH$_2$)$_{11}$—]; 1.0-2.0 [m, 52H, —(CH$_2$)$_{13}$; 4H, —N(—CH$_2$—CH$_2$—)$_2$; 6H, LysC$^\gamma$H$_2$; LysC$^\delta$H$_2$, LysC$^\beta$H$_2$]; 2.9-3.1 [m, 4H, —N(—CH$_2$—CH$_2$—)$_2$; 2H, LysC$^\omega$H$_2$; 2H, —N—CH$_2$—CH$_2$—NH—CO]; 3.4-3.6 [m, 2H, —N—CH$_2$—CH$_2$—NH—CO]; 3.9-4.3 [m, 2H, —CH$_2$—O—Si—; 1H, LysC$^\alpha$H]; 5.0-5.2 [m, —CH$_2$—C$_6$H$_5$; —NHZ]; 7.2-7.7 [m, 15H, —(C$_6$H$_5$)$_3$].

ES-MS: m/z: 830 [M+1]$^+$ for C$_{50}$H$_{92}$N$_4$O$_5$

Step (iii): The intermediate II prepared in above step (0.9 g, 0.93 mmol) and the intermediate prepared from mannose (0.7 g, 1.4 mmol, b, Scheme 3) were dissolved in dry DCM under nitrogen atmosphere and boron trifluoride ethyletherate (0.2 g, 1.4 mmol) was added at −20° C. The resultant solution left stirred at −20° C. for 2 h, diluted with excess chloroform and washed sequentially with saturated sodium bicarbonate (~3×50 mL) and water (~3×50 mL). The organic layer was dried over anhydrous sodium sulfate, filtered and the solvent from the filtrate removed by rotary evaporation. The residue upon column chromatographic purification with 100-200 mesh silica gel using 1-1.5% methanol in chloroform (v/v) as eluent afforded 0.5 g (51% yield) of the pure intermediate III. (R$_f$=0.5, 5% methanol in chloroform, v/v).

$^1$H NMR (300 MHz, CDCl$_3$): δ/ppm=0.9 [t, 6H, (CH$_3$—(CH$_2$)$_{13}$—)$_2$]; 1.2-1.9 [m, 52H, —(CH$_2$)$_{13}$; 4H, —N(—CH$_2$—CH$_2$—)$_2$; 6H, LysC$^\delta$H$_2$, LysC$^\beta$H$_2$, LysC$^\gamma$H$_2$]; 2.0-2.2 [4s, 12H, 4×—CO—CH$_3$]; 2.5-2.8 [m, 4H, —N(—CH$_2$—CH$_2$—)$_2$; 2H, —N—CH$_2$—CH$_2$—NH—CO]; 3.1-3.4 [m, 2H, LysC$^\omega$H$_2$; 2H, —N—CH$_2$—CH$_2$—NH—CO; 3H, 5-H]; 4.0-4.4 [m, 2H, NH—CO—CH$_2$—O—; 2H, —CH$_2$—OCOCH$_3$, 1H, LysC$^+$H]; 4.8 [s, 1H, 1-H]; 5.0 [s, —CH$_2$—C$_6$H$_5$]; 5.2-5.4 [m, 3H, 2-H, 3-H, 4-H]; 7.2-7.7 [m, 5H, —(C$_6$H$_5$)].

ES-MS: m/z: 1160 [M+1]$^+$ for C$_{64}$H$_{110}$N$_4$O$_{14}$.

Step (iv): The intermediate III prepared in above step (0.15 g, 0.12 mmol) was dissolved in 3 mL chloroform and 10 mL methyl iodide was added to the solution. The reaction mixture was stirred at room temperature for overnight and the solvent was removed on a rotary evaporator. The residue upon column chromatographic purification with silica gel (60-120 mesh size) and 2-2.5% methanol in chloroform (v/v) as eluent afforded 0.12 g (79% yield) of pure intermediate IV. (R$_f$=0.45, 5% methanol in chloroform, v/v).

$^1$H NMR (300 MHz, CDCl$_3$): δ/ppm=0.9 [t, 6H, 2×CH$_3$—(CH$_2$)$_{13}$—]; 1.2-1.5 [m, 52H, 2×—(CH$_2$)$_{13}$; 2H, LysC$^\gamma$H$_2$]; 1.7-1.9 [m, 4H, —N$^+$(—CH$_2$—CH$_2$—)$_2$; 2H, LysC$^\beta$H$_2$, 2H, LysC$^\delta$H$_2$]; 2.0-2.2 [4s, 12H, 4×-CO—CH$_3$]; 3.1-3.5 [m, 3H, —N$^+$—CH$_3$; 2H, LysC$^\omega$H$_2$; 4H—N$^+$(—CH$_2$—CH$_2$—)$_2$; 1H, 5-H]; 3.6-3.8 [m, 4H, —N$^+$—CH$_2$—CH$_2$—NH—CO—]; 4.0-4.4 [m, 2H, NH—CO—CH$_2$—O—; 2H, —CH$_2$—OCOCH$_3$]; 4.5 (dd, 1H, LysC$^+$H]; 4.8 [s, 1H, 1-H]; 5.0 [s, —CH$_2$—C$_6$H$_5$]; 5.2-5.4 [m, 3H, 2-H, 3-H, 4-H]; 7.2-7.7 [m, 5H, —(C$_6$H$_5$)].

ES-MS: m/z: 1174 [M]$^+$ for C$_{65}$H$_{113}$N$_4$O$_{14}$.

Step (v): The intermediate IV prepared in above step (0.12 g, 0.13 mmol) was dissolved in 8 mL methanol: acetic acid (1:1, v/v) and 2 drop of 2N hydrochloric acid. Pd(OH)$_2$/C (0.3 g) was added to the reaction mixture and air was removed. The resultant reaction mixture was stirred at 25° C. for 14 h under hydrogen atmosphere (2 atmos). The reaction mixture was filtered using celite and the filtrate was dried over anhydrous sodium sulphate and the solved removed by rotary evaporator afforded 0.08 g (75% yield) of the intermediate V. (R$_f$=~0.4, 20% methanol-chloroform, v/v).

ES-MS: m/z: 1040 [M]$^+$ for C$_{57}$H$_{107}$N$_4$O$_{12}$.

Step (vi) & (vii): The intermediate V prepared in above step (0.08 g, 0.08 mmol) was dissolved in 3 mL methanol and K$_2$CO$_3$ (0.7 g, 0.5 mmol) added to the reaction mixture 15, to increase the pH~9. The resultant solution was stirred at 25° C. for 2 h, neutralized with Amberlite IR120 (H$^+$), filtered and the filtrate was concentrated on rotary evaporator, followed by chloride ion exchange chromatography (using amberlyst A-26 chloride ion exchange resin). The final compound was recrystallized using MeOH & Acetone afforded 0.04 g (65% yield) of the pure target compound 3 (R$_f$=~0.3, 20% methanol-chloroform, v/v).

$^1$H NMR: (400 MHz, CDCl$_3$+CD$_3$OD): δ/ppm=0.9 [t, 6H, 2×CH$_3$—(CH$_2$)$_{13}$—]; 1.2-1.5 [m, 52H, 2×—(CH$_2$)$_{13}$]; 1.5-1.9 [4H, —N$^+$(—CH$_2$—CH$_2$—)$_2$; 6H, LysC$^\beta$H$_2$, LysC$^\gamma$H$_2$, LysC$^\delta$H$_2$]; 2.9-3.1 [m, 2H, LysC$^\omega$H$_2$; 3H, —N$^+$—CH$_3$; 4H—N$^+$(—CH$_2$—CH$_2$—)$_2$; 2H, —N$^+$—CH$_2$—CH$_2$—NH—CO—]; 3.5-4.0 [4H, 2-H, 3-H, 4-H, 5-H; 2H, —CH$_2$—OH; 2H, —N$^+$—CH$_2$—CH$_2$—NH—CO—]; 4.0-4.4 [m, 2H, —NH—CO—CH$_2$—O—; 1H, LysC$^+$H]; 4.9 [s, 1H, 1-H].

ES-MS: m/z: 872 [M]$^+$ for C$_{49}$H$_{99}$N$_4$O$_8$.

EXAMPLE 4

Evaluation of the Mannose Receptor Specific Gene Transfer Efficacies of Cationic Amphiphiles 1-3 in RAW 264.7 Cells.

Preparation of Plasmid DNA.

pCMV-SPORT-β-gal (cat., no. 10586-014 and was procured from Invitrogen Life Technologies™ Bangalore) and pCMV-Luc plasmids (cat. no. N8081S and was procured from New England Biolab Inc.) Plasmids were amplified in DH5α-strain of *Escherichia coli*, isolated by alkaline lysis procedure and finally purified by PEG-8000 precipitation as described previously (Karmali P P, et al. J Med Chem. 2004; 47:2123-2132). The purity of plasmid was checked by A$_{260}$/A$_{280}$ ratio (around 1.9) and 1% agarose gel electrophoresis.

Preparation of Liposomes.

The liposomes were prepared by the conventional method. Briefly, cationic lipids and co-lipids (Cholesterol, DOPE, DOPC) at 2:1 molar ratios were dissolved in chloroform. The solvent was then evaporated under a thin stream of nitrogen gas, vacuum dried for 8 h and hydrated in deionised water overnight to give a final lipid concentration of 1 mM for in vitro experiments or 5 mM for in vivo experiments. The hydrated lipid film was first vortexed for 30 seconds and then sonicated until clarity using a Branson 450 sonifier at 100% duty cycle and 25 W output power. The resulting clear aqueous liposomes were used in preparing lipoplexes.

Reporter Gene Expression Assay.

Cells were seeded at a density of 25000 (for RAW 264.7) per well in a 96-well plate for 18-24 h before the transfection. 0.3 µg (0.9 nmol) of plasmid DNA was complexed with varying amounts of lipids (1 nmol-8 nmol) in serum free medium (total volume made up to 100 µL) for 30 minutes. The charge ratios were varied from 1:1 to 8:1 over these ranges of the lipids. Immediately prior to transfection, cells plated in the 96-well plate were washed with PBS (2×100 µL) followed by the addition of lipoplexes. After 4 h of incubation, the medium was replaced with fresh complete medium containing 10% FBS. The luciferase reporter gene activity was estimated after 24 h. The cells were washed twice with PBS (100 pt each) and lysed in 50 µL lysis buffer. Care was taken to ensure complete lysis. 10 µL Promega luciferase assay buffer was added to the 5 µL lysate in a polystyrene plate and the luciferase activity per well was estimated using a FLx800 microplate luminescence reader (Bio-Tek instruments, INC, UK). Protein concentration in each well was determined by the modified Lowry method (Lundqvist A, et al. J Immunother. 2002, 25, 445-454) and the luciferase activity was expressed as the relative light unit (RLU) per mg of the protein.

Each transfection experiment was repeated two times on two different days. The transfection values reported were average values from two replicate transfection plates assayed on the same day. When mannan was used, the cells were pretreated for 30 mins at 37° C., 5% $CO_2$ with mannan (50 µg), and the transfection was carried out in its presence. After 4 h at 37° C., the medium was replaced with fresh complete medium without mannan and the transfection activity was evaluated after 24 h as described above.

Results.

The in vitro gene delivery efficiencies of representative cationic amphiphiles 1-3 (lipids 1-3) were evaluated in RAW 264.7 cells (a murine macrophage cell line) across the lipid: DNA charge ratios 8:1 to 1:1 using DOPE as a co-lipid and luciferase as the gene in the conventional reporter gene expression assay described above. The cationic amphiphiles containing shikimic (lipid 1) and quinic acid (lipid 2) acid head-groups showed higher in vitro transfection efficiencies than their control mannosylated lipid 3 across the lipid:DNA charge ratios 2:1 to 8:1 (FIG. 4). The transfection efficiencies of the lipids 1 and 2 and control lipid 3 were enhanced further when DOPC was used as a co lipid compared to using DOPE as a co-lipid at lipid:DNA charge ratio of 8:1 (FIG. 5). Such improved transfection efficiencies with DOPC is likely to provide enhanced antigen expression in bone marrow derived mouse APCs which are hard to transfect.

Next, we evaluated the mannose receptor specific gene delivery properties of the cationic amphiphiles 1-3 across the lipid:DNA ratio 8:1 to 1:1 using DOPE as a co-lipid in RAW 264.7 cells (as a model antigen presenting cell which express mannose receptor on their cell surface) in presence and in absence of mannan (a high affinity ligand for mannose receptor). The transfection efficiencies were found to be significantly diminished for the lipids 1, 2 and 3 when cells were pretreated with mannan. But the transfection efficiency of these lipids did not get affected in NIH3T3 cells (murine fibroblast cells does not express mannose receptor on cell surface) when the cells were pretreated with mannan (FIGS. 6-8). Similar results were observed in RAW cells as well as in NIH3T3 cells by using lipids 1, 2 and 3 in combination with DOPC as a co-lipid in 8:1 lipid:DNA charge ratio (FIG. 9). Thus, the findings summarized in FIGS. 6-9 convincingly demonstrated that the representative cationic amphiphiles 1, 2 and 3 (lipids 1, 2 and 3) of the present invention can deliver genes to APCs via mannose receptor.

EXAMPLE 5

Evaluation of the Mannose Receptor Specific Gene Transfer Efficacies of Cationic Amphiphiles 1-3 in Dendritic Cells.

Isolation of Dendritic Cells.

Primary mbmDCs were isolated using a previously described procedure (Inaba K, et al. J Exp Med 1992; 176: 1693-1702). Briefly, bone marrow collected from tibias and fibulas of male C57BL/6 mice was passed through a nylon mesh to remove bone and debris, and resuspended in complete DC medium (RPMI-1640 containing 10% FBS, 50 µM β-mercaptoethanol, 2 mM glutamine, 1% NEAA, 20 ng/mL GM-CSF and 10 ng/mL IL-4, 1% antibiotic solution). Cells were supplemented with fresh DC medium every two days. After 6 days, the aggregated cells were dislodged by gently pipetting RPMI over the adherent stroma. The dislodged cells were pulled together and centrifuged at 280 g for 10 mM at room temperature. The supernatant was discarded. The pellets were first resuspended in complete DC medium at $1\times10^6$ cells/mL and finally placed in 100 mm cell culture petri dishes at $1\times10^7$ cells/dish in 10 mL medium per dish. After 24 h, the nonadherent cells were collected by gently swirling the dish and were used for transfection and flow cytometry experiments. Cultures were maintained in a humidified atmosphere with 5% $CO_2$ at 37° C.

DC-Transfection.

First, the transfection efficiency of the lipids 1, 2 & 3 were evaluated in mouse bone marrow derived dendritic cells. To this end, the immature dendritic cells were isolated from the bone marrow of C57BL/6J mice by culturing with GM-CSF and IL-4 following the protocol described above. The immature dendritic cells were characterized for the standard DC-markers including MHC Class II, CD86, CD11c, CD40 and mannose receptors by treating the DCs with FITC/PE conjugated monoclonal antibodies for these DC markers. The profiles of the DC markers were monitored by flow cytometry. Findings in flow cytometry confirmed the characteristics of immature DCs having high intracellular levels of MHC class II molecules, low CD 86, high levels of CD11c, CD 40 and mannose receptor (FIG. 10). After confirming the presence of these expected DC markers on the surface of the isolated DCs, the transfection efficiencies of the cationic amphiphiles 1, 2 & 3 were evaluated in mbmDCs. The isolated DCs were seeded in 6 well plates with $1\times10^6$ cells per well. Lipoplexes containing 3 µg of plasmid DNA encoding green fluorescence protein (pα5GFP) and 8 nmol cationic amphiphiles 1, 2 & 3 were added to the cells and incubated for 4 h at 37° C. in serum free medium with 5% $CO_2$. After 4 h incubation, medium was replaced with complete DC medium and incubated for 18 h at 37° C. in presence of 5% $CO_2$. The transfection efficiencies of the cationic amphiphiles 1, 2 & 3 were measured by Flow cytometric analysis. The findings summarized in FIG. 11 clearly demonstrate that the efficacies of cationic amphiphiles 1 & 2 in delivering genes to dendritic cells are superior to those of their mannosyl analog 3. The findings in the fluorescence microscopic studies summarized in FIG. 12 provided further support for the proposition that the efficacies of cationic amphiphiles 1 & 2 in delivering genes to dendritic cells are superior to those of their mannosyl analog 3.

EXAMPLE 6

Induction of Humoral and Cellular Immune Responses in Dendritic Cell Based Genetic Immunizations.

Mice Immunization.

The transfected mbmDCs were harvested by DC isolation protocol described above and washed with PBS (2×100 μL). The cells were resuspended in HBSS medium at $5 \times 10^5$ cells/100 μL. 6-8 weeks old female C57BL/6J mice (n=5, each weighing 20-22 g) were immunized (s.c.) with 100 μL of transfected mbmDCs (~$5 \times 10^5$ cells) twice with a 7-day interval. Two weeks after the second immunization, mice were sacrificed and sera & spleens were collected for immune response assays.

Measurement of Anti β-gal Antibody by ELISA Assay (Humoral Response).

Anti-β-gal antibodies were measured using an enzyme linked immunosorbent (ELISA) assay as described earlier (McKeever, U. et al. Vaccine 2002; 20:1524-1531). Briefly, 96 well ELISA plates were coated with β-gal protein (0.3 μg per well) using a 5 μg/mL stock solution prepared in PBS. Plates were washed with PBS (3×200 μL) and blocked with 1% BSA in PBS at room temperature for 2 h. The plates were then washed with PBS containing 0.05% Tween-20 (3×200 μL) and incubated with mouse sera (100 μL) at room temperature for 2 h. The plates were again washed with PBS containing 0.05% Tween-20 (3×200 μL) and 100 μL of diluted (1:1000) anti-mouse antibody conjugated to horse radish peroxidase was added to each well. The plates were incubated at room temperature for 2 h and the unbound antibody-HRP conjugate was removed by washing the plates with PBS containing 0.05% Tween-20 (3×200 μL). The plates were then incubated in dark with 100 μL of ABTS (Calbiochem, USA) per well at 25° C. for 10 min and the absorbance was measured at 405 nm by ELISA reader (Bio-Tek instruments Inc, UK). The findings summarized in Part A, FIG. 13 demonstrate that administration of DCs pre-transfected with liposomes of cationic amphiphiles 1 & 2 elicited higher anti β-gal antibody responses than in case of administration of DCs pre-transfected with liposomes of the mannosyl analog 3. Stated differently, the findings summarized in Part A, FIG. 13 convincingly demonstrate that the immunization of mice with DCs pre-transfected with the complex of model DNA vaccine and liposomes of the presently disclosed cationic amphiables is capable of eliciting efficient antigen specific humoral immune response against the antigen encoded in the model DNA vaccine.

In situ IFN-γ (cellular immune response) and IL-4 (humoral immune response) by ELISA assays. CD4$^+$ Th cells exhibit their helper functions through secreted cytokines. Differences in cytokine secretion patterns among the two Th cell subsets (Th1 and Th2) determine the type of immune response mounted against a particular antigenic challenge. Th1 subset is responsible for mounting cell-mediated immune response e.g. activation of $T_C$ cells, while Th2 subset stimulates humoral responses, e.g. activation of antibody producing B cells. Two defining cytokines secreted by Th1 and Th2 cells are interferon gamma (INF-γ) and interleukin-4 (IL-4), respectively (Rengarajan, J. et al. Immunology Today 2000; 21:479-483). IFN-γ and IL-4 ELISA assays were performed as described previously (McKinney D M, et al. Journal of Immunological Methods 2000; 237:105). Two weeks after the last immunization, mice were sacrificed and their spleens were collected. Splenocytes were isolated by mincing the spleens with a syringe plunger and the erthrocytes were lysed with 1 mL of lysis buffer (0.14 M ammonium chloride in 0.02 M Tris.HCl, pH 7.2). The viable cells were counted by hemocytometer and used for Interferon-γ and IL-4 ELISA assays, immediately (without any in vitro restimulation). The assay was performed according to manufacturer's protocol (Endogen Mouse IFN-γ Elisa kit, and mouse IL-4 Elisa kit, Pierce Biotechnology, USA). Briefly, splenocytes were incubated in 96-well plates pre-coated with anti-mouse IFN-γ or anti-mouse IL-4 antibodies at $1 \times 10^6$ cells/well in 50 pt complete medium. The plates were covered and incubated for 12 h at 37° C. in presence of 5% $CO_2$. The cells were then washed out with wash buffer (3×200 μL) and 50 μL of the biotinylated secondary antibody was added to each well and incubated for 1 h at room temperature. The plates were washed with wash buffer (3×200 μL) and incubated with 100 μL of streptavidin-HRP solution for 30 min. The plates were again washed with wash buffer (3×200 μL), treated with 100 μL of TMB substrate solution and incubated for 30 min in dark. The reaction was stopped by adding 100 μL of stop solution and the absorbance was measured on a microplate reader at 450 nm.

ADVANTAGES OF THE PRESENT INVENTION

Lipids covered in our previously applied patents applications (Indian Patent Application No. 359/DEL/2006; International Patent Application No. PCT/IB 2007/000281, Publication No. WO/2008/001166, Publication date: Mar. 1, 2008) are 3-4 fold less efficient than the presently described lipids in transfecting dendritic cells. In addition, the presently described novel cationic amphiphiles with mannose-mimicking head-groups are efficacious in eliciting both cellular and humoral immune responses in dendritic cell based genetic immunization in mice and are therefore likely to find future applications in the area of DNA vaccination.

We claim:

1. Cationic amphiphiles with mannose-mimicking acid head-groups having the general formula A

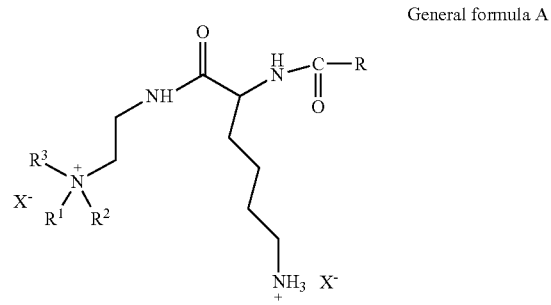

General formula A wherein

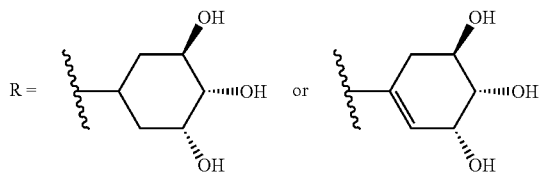

wherein $R^1$ and $R^2$ is independently hydrogen or a lipophilic moiety containing at least eight carbon atoms and is optionally selected from 8-24 carbon containing alkyl, mono-, di- and tri-unsaturated alkenyl ($C_8$-$C_{22}$) provided both $R^1$ and $R^2$ are not hydrogen;

R³ is independently hydrogen or alkyl ($C_1$-$C_5$, straight or branched) or hydroxy or amino-alkyl functional groups ($C_1$-$C_5$, straight or branched); and X is optionally selected from chlorine or bromine atom.

2. The cationic amphiphile of claim 1, wherein lipophilic R¹ and R² moiety is selected from the group consisting of saturated $C_8$-$C_{22}$ alkyl groups and unsaturated $C_8$-$C_{22}$ alkenyl groups containing 1, 2 or 3 double bonds.

3. A process for the synthesis of cationic amphiphiles with mannose-mimicking acid head-groups of general formula A General formula A

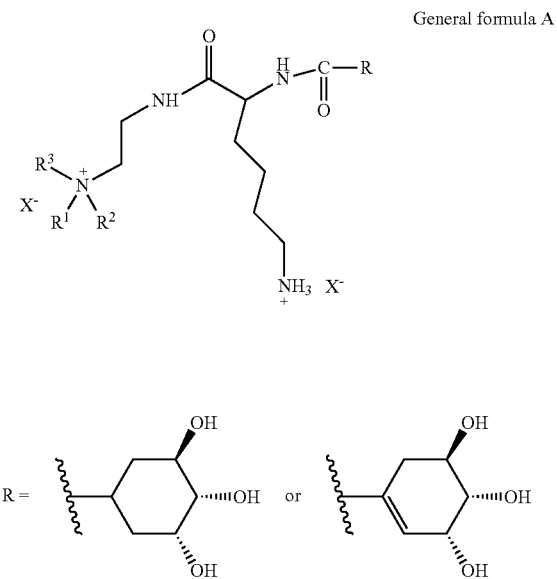

wherein each of R¹ and R² is independently hydrogen or a lipophilic moiety containing at least eight carbon atoms and is optionally selected from 8-24 carbon containing alkyl, mono-, di- and tri-unsaturated alkenyl ($C_8$-$C_{22}$) provided both R¹ and R² are not hydrogen;

R³ is independently hydrogen or alkyl ($C_1$-$C_5$, straight or branched) or hydroxy or amino-alkyl functional groups ($C_1$-$C_5$, straight or branched);

X is optionally selected from chlorine or bromine atom, said process comprising the steps of:

(a) coupling a mixed primary-tertiary lipophilic aliphatic alkyl protected amine containing saturated or unsaturated aliphatic hydrocarbon chains with shikimic or quinic acids in polar aprotic solvent, in presence of amide bond forming reagent selected from group ethylenedicarbodiimide (EDCI) and N-hydroxybenzotriazole (HOBt) at 0-80° C. to obtain the corresponding aliphatic hydrophobic amide intermediate;

(b) quaternizing the protected hydrophobic amide obtained in step (a) with alkyl iodides to obtain the corresponding protected quaternized amphiphilic ammonium iodide intermediate; and deprotecting of protected quaternized amphiphilic ammonium iodide intermediate as obtained in step (b) followed by ion exchange chromatography on halide ion exchange resin and mixed polar organic solvent as the eluent to obtain compounds of general formula A.

4. The process of claim 3, wherein saturated or unsaturated aliphatic hydrocarbon chains of said amine have 8-22 carbon atoms.

5. The process of claim 3, wherein the polar aprotic solvent used in step (a) is selected from the group consisting of dichloro methane (DCM), dimethyl formamide (DMF), dimethylsulfoxide, pyridine, and triethyl amine.

6. The process of claim 3, wherein quaternization of the intermediate hydrophobic amide obtained in step (a) is carried out at a temperature between 25-30° C.

7. The process of claim 3, wherein the organic solvent used as polar eluent in step (c) is selected from the group consisting of methanol, ethanol, chloroform, dichloro methane and ethyl acetate.

8. The process of claim 3, wherein the halide ion exchange resins used in step (c) is selected from the chloride and bromide ion exchange resins.

9. A formulation comprising the cationic amphiphiles of claim 1, in pure form or in combination with co-lipids and polyanionic compounds preferably nucleic acids along with physiologically acceptable additives.

10. The formulation of claim 9, wherein the co-lipid is selected from sterol group or a neutral phosphatidyl ethanolamine or neutral phosphatidyl choline.

11. The formulation of claim 10, wherein the co-lipid is selected from the group consisting of cholesterol, dioleyolphosphatidylethanolamine (DOPE), and dioleyolphosphatidylcholine (DOPC).

12. The formulation of claim 9, wherein the co-lipid is preferentially selected from dioleyolphosphatidylcholine (DOPC) or cholesterol.

13. The formulation of claim 9, wherein the molar ratio of the cationic amphiphile to co-lipid used is in the range of 1:1 to 1:3.

14. The formulation of claim 13, wherein the molar ratio of the cationic amphiphile to co-lipid used is 1:1.

15. The formulation of claim 9, wherein the polyanionic compounds are biologically active compounds selected from the group consisting of nucleic acids that encode for a therapeutically important immunogen, protein, nucleic acid, an oligonucleotide, a peptide or a protein or a drug.

16. The formulation of claim 15, wherein the nucleic acid is selected from the group of a circular or linear plasmid or is a ribonucleic acid, a ribosomal RNA, antisense polynucleotide of RNA or DNA, polynucleotide of genomic DNA, cDNA or mRNA.

17. The formulation of claim 15, wherein the polyanionic compounds are used singly or in combination thereof.

18. The formulation of claim 9, wherein the said formulation comprises amount of cationic amphiphiles in the range of 9.0 to 0.3 microgram and lipid to DNA charge ratios ranging from 0.3:1 to 9:1.

19. A transfection complex comprising of the formulation of claim 9.

20. A method for producing immune response, comprising:

(a) administering the transfection complex as claimed in claim 19 containing at least one cationic amphiphile with a polynucleotide wherein the said polynucleotide encodes an immunogen to at least one mouse thereby generating at least one immunized mouse; and (b) measuring the monoclonal antibodies produced in mouse body.

* * * * *